US012703837B2

(12) United States Patent
Natoli et al.

(10) Patent No.: US 12,703,837 B2
(45) **Date of Patent: *Aug. 11, 2026**

(54) TREATMENT COMPOSITIONS WITH MODIFIED AMINO ACID MULTIMERS

(71) Applicant: The Procter & Gamble Company, Cincinnati, OH (US)

(72) Inventors: Sean N. Natoli, Liberty Township, OH (US); Gregory Scot Miracle, Liberty Township, OH (US); Rajan Keshav Panandiker, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 509 days.

This patent is subject to a terminal disclaimer.

(21) Appl. No.: 18/096,119

(22) Filed: Jan. 12, 2023

(65) Prior Publication Data

US 2023/0220300 A1 Jul. 13, 2023

Related U.S. Application Data

(60) Provisional application No. 63/299,030, filed on Jan. 13, 2022.

(51) Int. Cl.

| | |
|---|---|
| ***C11D 3/32*** | (2006.01) |
| ***A61K 8/44*** | (2006.01) |
| ***C11D 1/10*** | (2006.01) |
| ***C11D 3/26*** | (2006.01) |
| ***C11D 3/30*** | (2006.01) |
| ***C11D 3/33*** | (2006.01) |
| ***C11D 3/37*** | (2006.01) |
| ***C11D 3/50*** | (2006.01) |
| ***C11D 7/32*** | (2006.01) |

(52) U.S. Cl.

CPC ................. *C11D 1/10* (2013.01); *A61K 8/44* (2013.01); *C11D 3/26* (2013.01); *C11D 3/30* (2013.01); *C11D 3/33* (2013.01); *C11D 3/37* (2013.01); *C11D 3/50* (2013.01); *C11D 3/507* (2013.01); *C11D 7/3245* (2013.01)

(58) Field of Classification Search

CPC .... C11D 3/26; C11D 3/30; C11D 3/33; C11D 3/37; C11D 3/50; C11D 3/507; C11D 7/3245

USPC ......................... 510/101, 475, 477, 488, 499

See application file for complete search history.

(56) References Cited

U.S. PATENT DOCUMENTS

| | | | |
|---|---|---|---|
| 5,204,023 | A | 4/1993 | Behan et al. |
| 5,912,002 | A | 6/1999 | Grieveson et al. |
| 6,413,920 | B1 | 7/2002 | Bettiol |
| 7,572,938 | B2 | 8/2009 | Derrer et al. |
| 7,867,961 | B2 | 1/2011 | Tobita |
| 7,935,669 | B2 | 5/2011 | Fehr et al. |
| 8,287,844 | B2 | 10/2012 | Burgo |
| 8,906,843 | B2 | 12/2014 | Smith et al. |
| 9,326,928 | B2 | 5/2016 | Tong et al. |
| 10,552,557 | B2 | 2/2020 | Frankenbach et al. |
| 2003/0073607 | A1 | 4/2003 | Smets et al. |
| 2003/0171250 | A1 | 9/2003 | Smets et al. |
| 2003/0211963 | A1 | 11/2003 | Bettiol et al. |
| 2005/0009727 | A1 | 1/2005 | Bettiol et al. |
| 2009/0275630 | A1 | 11/2009 | Provost et al. |
| 2010/0135936 | A1 | 6/2010 | Dueva-koganov et al. |
| 2012/0065114 | A1 | 3/2012 | Bettiol et al. |
| 2013/0089587 | A1 | 4/2013 | Staudigel et al. |
| 2015/0140052 | A1 | 5/2015 | Gizaw et al. |
| 2018/0193233 | A1 | 7/2018 | Burgo |
| 2020/0032167 | A1 | 1/2020 | Qin et al. |
| 2020/0239811 | A1 | 7/2020 | Burgo |
| 2020/0368164 | A1 | 11/2020 | Becker et al. |
| 2021/0139816 | A1 | 5/2021 | Miracle et al. |
| 2022/0403297 | A1 | 12/2022 | Natoli et al. |
| 2023/0002330 | A1 | 1/2023 | Natoli et al. |

FOREIGN PATENT DOCUMENTS

| | | | |
|---|---|---|---|
| CN | 106436323 | A | 2/2017 |
| EP | 0310299 | A1 | 4/1989 |
| EP | 0392619 | A2 | 10/1990 |
| EP | 3733824 | A1 | 11/2020 |
| JP | 2004010553 | A | 1/2004 |
| JP | 2019150783 | A | 9/2019 |
| JP | 2020083844 | A | 6/2020 |
| WO | 0071658 | A1 | 11/2000 |
| WO | 200127234 | A1 | 4/2001 |
| WO | 2001051599 | A1 | 7/2001 |
| WO | 2008106214 | A1 | 9/2008 |
| WO | 2013150044 | A2 | 10/2013 |
| WO | 2019079313 | A1 | 4/2019 |

(Continued)

OTHER PUBLICATIONS

All Office Actions: U.S. Appl. No. 18/295,910, filed Apr. 5, 2023.

Andreas Herrmann, "Controlled Release of Volatiles under Mild Reaction Conditions: From Nature to Everyday Products", vol. 46, 2007, pp. 5836-5863.

Pinazo et al. "Amino acid-based surfactants: New antimicrobial agents", Advances in Colloid and Interface Science, Dec. 15, 2015, pp. 17-39.

Pérez et al. "Gemini surfactants from natural amino acids", Advances in Colloid and Interface Science, Oct. 24, 2013, pp. 134-155.

Qing-Yi et al. "The antimicrobial activities of the cinnamaldehyde adducts with amino acids", International Journal of Food Microbiology, Aug. 4, 2011, pp. 164-170.

(Continued)

*Primary Examiner* — Gregory R Delcotto

(74) *Attorney, Agent, or Firm* — Carolyn S. Powell; Andrew J. Mueller

(57) ABSTRACT

Treatment compositions that include modified amino acid multimer compounds, which may be useful for delivering certain benefit agents such as perfume raw materials or antibacterial agents. The present disclosure also relates to methods of making and using such compounds and compositions. The present disclosure also relates to related precursor compounds and premix compositions.

20 Claims, No Drawings

(56) References Cited

FOREIGN PATENT DOCUMENTS

| | | | | | |
|---|---|---|---|---|---|
| WO | WO-2019094913 | A2 * | 5/2019 | ............... | A61K 8/64 |
| WO | 2020104009 | A1 | 5/2020 | | |
| WO | 2020224767 | A1 | 11/2020 | | |
| WO | 2020227038 | A1 | 11/2020 | | |
| WO | 2021064068 | A1 | 4/2021 | | |
| WO | 2001032848 | A1 | 5/2021 | | |

OTHER PUBLICATIONS

Tripathy et al., "Synthesis, chemistry, physicochemical properties and industrial applications of amino acid surfactants: A review", Comptes Rendus Chimie, Feb. 3, 2018, pp. 112-130.
Unpublished U.S. Appl. No. 18/295,910, filed Apr. 5, 2023, Gregory Scot Miracle et al.
Search Report and Written Opinion for PCT/US2023/060600 dated Mar. 31, 2023, 10 pages.
All Office Actions; U.S. Appl. No. 18/096,109, filed Jan. 12, 2023.
Unpublished U.S. Appl. No. 18/096,109, filed Jan. 12, 2023, to Sean N. Natoli et al.

* cited by examiner

TREATMENT COMPOSITIONS WITH MODIFIED AMINO ACID MULTIMERS

FIELD OF THE INVENTION

The present disclosure relates to treatment compositions that include modified amino acid multimer compounds, which may be useful for delivering certain benefit agents such as perfume raw materials or antibacterial agents. The present disclosure also relates to methods of making and using such compounds and compositions. The present disclosure also relates to related precursor compounds and premix compositions.

BACKGROUND OF THE INVENTION

Many treatment compositions, such as those suitable for treating fabrics, include a variety of benefit agents, such as perfume, that provide benefits in the end use of the products. Many of these benefit agents are intended to deposit onto a target surface, such as fabric. It is therefore useful and desirable to increase the deposition efficiency of such benefit agents, as well as their release profiles.

The deposition of such benefit agents may conveniently be facilitated by deposition aids and/or carrier materials, but several factors go into the selection of a suitable material. For example, the selected material must result in an improved deposition profile compared to the benefit agent that they are intended to deliver, which is particularly challenging in aqueous treatment environments, such as in the wash and/or rinse cycle of an automatic laundry machine. For sustainability reasons, it may be desirable that such materials are naturally derived and/or are biodegradable. Additionally, it is desirable for such materials to have suitable loading efficiency of the benefit agent to be delivered, as well as an appropriate rate of release of the benefit agent once deposited. It may further be desired that such materials are capable of interacting with a diverse set of benefit agents, and/or be capable of being conveniently incorporated into a product formulation in a variety of ways.

Thus, there is a need for improved ingredients in treatment compositions that can efficiently deposit onto target surfaces and release benefit agents, particularly when used in aqueous environments. It is further preferred that such ingredients are derived (at least in part) from naturally sourced materials.

SUMMARY OF THE INVENTION

The present disclosure relates to treatment compositions that include a treatment adjunct and a modified amino acid multimer compound that can be useful for delivering certain benefit agents.

For example, the present disclosure relates to a treatment composition comprising: a treatment adjunct; and a modified amino acid multimer compound, wherein the multimer compound comprises a central linking group and from two to six amino acid portions each covalently linked to the central linking group by a heteroatom selected from the group consisting of O, S, and N, preferably O, wherein the central linking group comprises from 3 to 18 carbon atoms, wherein each amino acid portion comprises a carbon backbone comprising one or more carbon atoms, a carbonyl group that comprises a carbon atom, and a nitrogen atom, wherein the heteroatom is directly bonded to the carbon atom of the carbonyl group and to the central linking group, wherein at least one amino acid portion comprises an organic moiety covalently bonded to the nitrogen atom of the amino acid portion, wherein the organic moiety comprises a benefit agent residue, wherein when one or more bonds that connect the benefit agent residue to the amino acid portion are cleaved, a benefit agent is released, wherein the benefit agent comprises an aldehyde moiety, a ketone moiety, or a combination thereof.

The present disclosure also relates to a treatment composition comprising: a treatment adjunct; and a modified amino acid multimer compound, wherein the multimer compound comprises a central linking group and from two to six amino acid portions each covalently linked to the central linking group, wherein the central linking group comprises from 3 to 18 carbon atoms, wherein each amino acid portion comprises a carbonyl group at a C terminus, wherein the carbonyl group comprises a carbon atom, wherein the carbon atom of the carbonyl is bonded to a heteroatom of the central linking group, wherein the heteroatom is selected from the group consisting of O, S, or N, wherein each amino acid portion further comprises a nitrogen atom at an N terminus, wherein at least one amino acid portion comprises a benefit agent residue that is bonded to the nitrogen atom at the N terminus of the at least one amino acid portion, wherein a benefit agent is released when one or more bonds that connect the benefit agent residue to the amino acid portion are cleaved, wherein the benefit agent comprises an aldehyde moiety, a ketone moiety, or a combination thereof.

The present disclosure also relates to a treatment composition comprising: a treatment adjunct, and a modified amino acid multimer compound, wherein the modified amino acid multimer compound is characterized by a structure according to Formula I:

$$L[E]_t \quad \text{Formula I,}$$

wherein t is independently an integer from 2 to 6, preferably 2 to 5, more preferably 2 to 4, more preferably 2 to 3, more preferably 2; wherein L is a central linking group that is multivalent and that comprises 3 to 18 carbon atoms; wherein each E group is independently selected from -GH, -GX, or a moiety according to Formula II:

Formula II

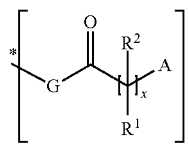, with the proviso that the multimer compound comprises at least two E groups that are moieties according to Formula II, wherein * indicates the point of attachment of the E group with L, wherein the value of x is from 1 to 9, preferably from 1 to 6, more preferably from 1 to 3, even more preferably from 1 to 2, even more preferably 1, wherein each G is independently selected from the group consisting of —O—, —N($R^3$)—, or —S—, preferably wherein each G group is the same, wherein each $R^3$, if present, is independently selected from H or a monovalent moiety with a molecular weight between 14 and 881 Da, preferably between 41 and 255 Da, wherein X, if present, is a suitable charge-balancing counterion, wherein each $R^1$ is independently selected from H or a monovalent moiety with a molecular weight between 15 and 507 Da, preferably $R^1$ is selected from a side group of a proteogenic amino acid or a monovalent moiety with a molecular weight between 15 and 142 Da; wherein each $R^2$ is independently selected from H and a monovalent moiety with a molecular weight of between 15 and 1000 Da, preferably from 15 to 507 Da, more preferably from 15 to 142 Da, preferably wherein $R^2$ is H, wherein each A group is a monovalent nitrogen-comprising moiety, wherein at least one A group comprises an independently selected benefit agent residue that is linked to the rest of the A group by one or more bonds, wherein a benefit agent is released when the one or more bonds are cleaved, wherein the benefit agent comprises an aldehyde moiety, a ketone moiety, or a combination thereof.

The present disclosure also relates to a modified amino acid multimer compound as described herein.

The present disclosure also relates to a modified amino acid multimer precursor compound having a structure according to Formula I', $$L[E]_t \quad \text{Formula I'},$$

wherein L, E, and t are defined as above, with the proviso that the multimer precursor compound comprises at least two E groups that are moieties according to Formula II as defined above, with the further proviso that each A group of the moieties according to Formula II are selected from: (a) $H_2N$—, or (c) $HG'(J)_dN(H)$—, wherein G', J, and d are defined as above.

The present disclosure also relates to a premix composition comprising a modified amino acid multimer precursor compound, a benefit agent, and optionally water, wherein the benefit agent comprises an aldehyde moiety, a ketone moiety, or a combination thereof; wherein the premix composition optionally further comprises a non-aqueous solvent, more preferably a hydroxyl-containing solvent, even more preferably ethanol.

The present disclosure also relates to a method of making a treatment composition as described herein, wherein the method comprises at least one of the following: (a) combining a modified amino acid multimer compound with an adjunct ingredient, preferably wherein the adjunct ingredient is part of a base composition; (b) combining a premix composition with an adjunct ingredient, preferably wherein the adjunct ingredient is part of a base composition; (c) combining a modified amino acid multimer precursor compound, a benefit agent, and an adjunct ingredient, preferably wherein the adjunct ingredient is part of a base composition and the modified amino acid multimer compound and the benefit agent are each added to the base composition as separate inputs.

The present disclosure also relates to a method of treating an article or a surface, wherein the method comprises treating the article or surface with a treatment composition as described herein, optionally in the presence of water, optionally further including the step of rinsing and/or drying the article or surface.

DETAILED DESCRIPTION OF THE INVENTION

The present disclosure relates to treatment compositions that include modified amino acid multimer compounds that facilitate the deposition and release of benefit agents. Thus, the amino acid multimer compounds of the present disclosure may be considered "pro-benefit-agent compounds," such as pro-perfume compounds.

The modified amino acid multimer compounds of the present disclosure (also "multimer compounds" or even simply "multimers," as used herein) include at least two amino acid portions that are covalently bonded together, for example by a central linking group. The central linking group is preferably relatively hydrophobic, which may help to improve the deposition profile of the compound onto a target surface, particularly in aqueous treatment environments and/or onto hydrophobic surfaces.

Furthermore, the multimer compounds of the present disclosure include the residues of one or more benefit agents, which are released over time, preferably once the multimer compound deposits onto a target surface, such as a fabric. The benefit agents that form the residues include an aldehyde or ketone moiety which reacts with the amine group of the amino acid portions. When the bond cleaves, the benefit agent is released.

The multimer compounds of the present disclosure provide more options for modification and loading efficiency compared to single amino acids. For example, a single multimer compound may conveniently carry the residues of at least two benefit agents via the usage of a single central linking group. Without wishing to be bound by theory, it is believed that through selection of the central linking group and/or the side groups of the amino acid portions (e.g., for hydrophobicity), the manufacturer may accordingly "tune" the multimers accordingly to get a desired performance profile depending on the formulation and intended use of the treatment composition.

The compounds, compositions, and related processes of the present disclosure are discussed in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

As used herein, the phrase "chain atoms" means the sum of all atoms in an indicated group or moiety, excluding hydrogen atoms. The chain atoms may be in a linear configuration, a branched configuration, and/or a ring configuration.

As used herein, a "peptide bond" means a bond between the C terminus of one amino acid (or derivative thereof) and the N terminus of another amino acid (or derivative thereof). As used herein, the phrase "does not include a peptide bond" is not intended to preclude the presence of a general amide bond, other than when the amino acids (or derivatives thereof) are in the described C terminus/N terminus orientation. The multimers of the present disclosure are typically not intended to include dipeptides, as such materials tend to have reduced loading capacity for benefit agent residue. The reduced loading capacity generally results from one fewer nitrogen being available for benefit agent loading, as in a dipeptide, a nitrogen of the N terminus of one amino acid is typically bonded to the carbon of the carbonyl of the C terminus of another.

As used herein, an amino acid "multimer," modified or otherwise, means a compound having more than one amino acid portion as described herein. Typically, such materials will comprise from two to six amino acid portions; for clarity, a "multimer" as used herein may have only two amino acid portions. However, the multimers of the present disclosure are not understood to be di-, tri-, or polypeptides, due to a difference in arrangement.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Treatment Compositions

The present disclosure relates to treatment compositions. The treatment compositions typically comprise a treatment adjunct and a modified amino acid multimer compound, each of which is discussed in more detail below.

The treatment compositions may be consumer product compositions. The consumer products compositions of the present disclosure may be useful in baby care, beauty care, fabric care, home care, family care, feminine care, and/or health care applications. The treatment compositions may be useful for treating a surface, such as fabric, hair, or skin. The consumer product compositions may be intended to be used or consumed in the form in which it is sold. The consumer product compositions may be not intended for subsequent commercial manufacture or modification.

The treatment composition may be a household care composition. The treatment composition may be a fabric care composition, a hard surface cleaner composition, a dish care composition, a hair care composition (such as shampoo or conditioner), a body cleansing composition, or a mixture thereof, preferably a fabric care composition.

The treatment composition may be a fabric care composition, such as a laundry detergent composition (including a heavy-duty liquid washing detergent or a unit dose article), a fabric conditioning composition (including a liquid fabric softening and/or enhancing composition), a laundry additive, a fabric pre-treat composition (including a spray, a pourable liquid, or a spray), a fabric refresher composition (including a spray), or a mixture thereof.

The treatment composition may be a beauty care composition, such as a hair treatment product (including shampoo and/or conditioner), a skin care product (including a cream, lotion, or other topically applied product for consumer use), a shave care product (including a shaving lotion, foam, or pre- or post-shave treatment), personal cleansing product (including a liquid body wash, a liquid hand soap, and/or a bar soap), a deodorant and/or antiperspirant, or mixtures thereof.

The treatment composition may be a home care composition, such as an air care, car care, dishwashing, hard surface cleaning and/or treatment, and other cleaning for consumer or institutional use.

The treatment composition may be in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam/mousse, a non-woven sheet, or a mixture thereof.

The treatment composition may be in the form of a liquid. The liquid composition may include from about 30%, or from about 40%, or from about 50%, to about 99%, or to about 95%, or to about 90%, or to about 75%, or to about 70%, or to about 60%, by weight of the composition, of water. The liquid composition may be a liquid laundry detergent, a liquid fabric conditioner, a liquid dish detergent, a hair shampoo, a hair conditioner, or a mixture thereof.

The treatment composition may be in the form of a solid. The solid composition may be a powdered or granular composition. Such compositions may be agglomerated or spray-dried. Such composition may include a plurality of granules or particles, at least some of which include comprise different compositions. The composition may be a powdered or granular cleaning composition, which may include a bleaching agent. The composition may be in the form of a bead or pastille, which may be pastilled from a liquid melt. The composition may be an extruded product.

The treatment composition may be in a particulate form, such as a plurality of particulates. Individual particulates may have a mass from about 1 mg to about 1 g. The emulsion may be dispersed in a water-soluble carrier. The water-soluble carrier may be selected from the group consisting of polyethylene glycol, sodium acetate, sodium bicarbonate, sodium chloride, sodium silicate, polypropylene glycol polyoxoalkylene, polyethylene glycol fatty acid ester, polyethylene glycol ether, sodium sulfate, starch, and mixtures thereof. The water-soluble carrier may be a water-soluble polymer. The treatment composition, when in particulate form, may comprise from about 25 wt % to about 99.99 wt % of the water-soluble carrier, and from about 0.001 wt % to about 50 wt % by weight of a multimer compound according to the present disclosure. The particulate form may be in the form of a bead or pastille.

The treatment composition may be in the form of a unitized dose article, such as a tablet, a pouch, a sheet, or a fibrous article. Such pouches typically include a water-soluble film, such as a polyvinyl alcohol water-soluble film, that at least partially encapsulates a composition. Suitable films are available from MonoSol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch or compartments thereof may be liquid, solid (such as powders), or combinations thereof. Pouched compositions may have relatively low amounts of water, for example less than about 20%, or less than about 15%, or less than about 12%, or less than about 10%, or less than about 8%, by weight of the detergent composition, of water.

The treatment composition may be in the form of a spray and may be dispensed, for example, from a bottle via a trigger sprayer and/or an aerosol container with a valve.

The treatment composition may have a viscosity of from 1 to 1500 centipoises (1-1500 mPa·s), from 100 to 1000 centipoises (100-1000 mPa·s), or from 200 to 500 centipoises (200-500 mPa·s) at 20 $s^{-1}$ and 21° C.

Modified Amino Acid Multimer Compounds

The present disclosure relates to modified amino acid multimer compounds, which typically comprise from two to six amino acid portions covalently bonded to a central linking group. Such compounds typically do not include peptide bonds, although amide bonds may be present in some cases. The multimer compounds comprise at least one benefit agent residue, preferably at least two benefit agent residues. The multimer compounds are capable of depositing onto a target surface, thereby bringing the benefit agent residue to the target surface. When the bond holding the residue is cleaved, the benefit agent releases. The release of the benefit agent may be triggered by any suitable mechanism, such as the presence of water or heat, preferably water, particularly when the linking bond is an imine bond. The bond may cleave under ambient conditions over the passage of time. The released benefit agents typically comprise an oxygen-containing moiety, namely an aldehyde moiety and/or a ketone moiety. As further described herein, the central linking group may comprise one or more hydrophobic moieties, which can facilitate improved deposition and/or performance efficiency.

Such multimer compounds may be part of a treatment composition, as described herein. The treatment composition may comprise from about 0.001% to about 30%, preferably from about 0.001% to about 20%, more preferably from about 0.001% to about 15%, 0.001% to about 10%, preferably from about 0.01% to about 5%, by weight of the treatment composition, of the modified amino acid multimer compound. The treatment composition may comprise the modified amino acid multimer compound in an amount sufficient to deliver from about 0.01% to about 10%, preferably from about 0.1% to about 5%, by weight of the treatment composition, of the benefit agent that is to be released by the multimer compound.

The modified amino acid multimer compounds of the present disclosure comprise a central linking group and from two to six amino acid portions covalently linked to the central linking group by a heteroatom selected from the group consisting of O, S, and N, preferably O, where the central linking group comprises from 3 to 18 carbon atoms, where the central linking group may be a divalent, trivalent, tetravalent, pentavalent, or hexavalent organic moiety, where wherein each amino acid portion comprises a carbon backbone comprising one or more carbon atoms, a carbonyl group that comprises a carbon atom, and a nitrogen atom, where the heteroatom is directly bonded to the carbon atom of the carbonyl group and to the central linking group, where at least one amino acid portion comprises an organic moiety covalently bonded to the nitrogen atom of the amino acid portion, where the organic moiety comprises a benefit agent residue, where when one or more bonds that connect the benefit agent residue to the amino acid portion are cleaved, a benefit agent is released, where the benefit agent comprises an aldehyde moiety, a ketone moiety, or a combination thereof.

The modified amino acid multimer compound may comprise a central linking group and from two to six amino acid portions covalently linked to the central linking group, typically by non-peptide covalent bonds; where the central linking group comprises from 3 to 18 carbon atoms, where the central linking group may be a divalent, trivalent, tetravalent, pentavalent, or hexavalent organic moiety, where each amino acid portion comprises a carbonyl group at a C terminus, where the carbonyl group comprises a carbon atom, where the carbon atom of the carbonyl is bonded to a heteroatom of the central linking group, where the heteroatom is selected from the group consisting of O, S, or N, where each amino acid portion further comprises a nitrogen atom at an N terminus, where at least one amino acid portion comprises a benefit agent residue that is bonded to the nitrogen atom at the N terminus of the at least one amino acid portion, where a benefit agent is released when one or more bonds that connect the benefit agent residue to the amino acid portion are cleaved, wherein the benefit agent comprises an aldehyde moiety, a ketone moiety, or a combination thereof. For clarity, the C terminus of each amino acid portion is proximal to the central linking group, and the N terminus is distal to the central linking group.

As mentioned above, the modified amino acid multimer multimer compound comprises at least two amino acid portions that are covalently connected to a central linking group. The multimer compounds, including each amino acid portion, are typically derived from amino acids. Proteinogenic amino acids may be a preferred starting material, as such compounds are attractive for environmental or sustainability reasons, as they tend to be naturally occurring. For most naturally-occurring amino acids, the stereogenic carbon alpha to the amino group has the L-configuration. D-Amino acids are occasionally found in nature. While either L- or D-Amino acids as well as mixtures may be used, economic factors may lead to a preference for the more abundant L-Amino acids. Relatedly, biosynthesized amino acids may be preferred.

Each amino acid portion may comprise a carbon backbone. The carbon backbone may be part of a carbon-containing core, which may also comprise one or more side groups, a nitrogen atom, and a carbonyl group. The carbon backbone is understood to not include the carbons of the carbonyl-containing moiety or the side group(s), if any. The carbon backbone of each amino acid portion may each independently comprise from 1 to 9 carbon atoms, preferably from 1 to 6 carbon atoms, preferably from 1 to 3 carbon atoms, more preferably 1 to 2 carbon atoms, even more preferably 1 carbon atom. Relatively fewer carbon atoms may be preferred for mass-efficiency reasons. In particular, backbones comprising only one carbon atom may be preferred because such structures are indicative of naturally-occurring, proteinogenic amino acids.

The carbon-containing core may be derived from an amino acid. Preferably, the core is derived from a proteinogenic amino acid. In particular, naturally-derived or biosynthesized amino acids may be preferred. Such materials may be preferred for environmental/sustainability reasons, and because they tend to be readily available at reasonable costs.

The at least one side group of a parent amino acid from which an amino acid portion is derived may be selected from a hydrogen or a suitable organic group, preferably hydrogen or an organic group having from one to about eighteen atoms, preferably carbon atoms. The at least one side group may comprise one or more functional groups, such as carboxyl groups, amine groups, thiol groups, or hydroxyl groups. The at least one side group may be linear or branched. The at least one side group may comprise an aryl ring. The amino acid preferably may comprise only one non-hydrogen side group (e.g., only one organic group). The amino acid may comprise more than one non-hydrogen side group. The at least one side group preferably comprises the side group of a proteinogenic amino acid. The carbon-containing core may comprise at least one side group that is a hydrogen, and at least one side group that is an organic group. All of the side groups may be hydrogen, for example when the amino acid portion is based on or otherwise derived from glycine.

At least one, preferably at least two, more preferably all, of the amino acid portions are derived from proteogenic amino acids, preferably proteogenic amino acids independently selected from cysteine, glycine, aspartic acid, glutamic acid, lysine, or combinations thereof, more preferably cysteine. The amino acids may be selected for advantageous reactivity and/or deposition profiles.

At least two, preferably all, of the amino acid portions may be derived from amino acids having the same identity, preferably derived from proteogenic amino acids having the same identity. For example, the amino acid portions may be derived from cysteine. Forming multimers from amino acids of the same identity can facilitate convenient and/or predictable reactions (e.g., the amino acid portions are substantially the same).

One way in which the multimer compounds of the present disclosure are "modified" amino acid multimers is that the amino acid portions are bonded to a central linking group at the respective C terminus portions of the amino acid portions (e.g., the end having the carbonyl group).

For example, as described above, each amino acid portion comprises a carbonyl group, which typically is/was part of the carboxyl group of the parent amino acid. The carbonyl group comprises a carbon atom that is double-bonded to an oxygen atom (C═O). Typically, the carbon atom of the carbonyl group is directly bonded to a heteroatom selected from O, S, or N.

The heteroatom is typically part of the central linking group. The heteroatom of the central linking group may be bonded to a carbon atom of an amino acid portion through any suitable reaction. For example, the (parent) amino acids of one or more amino acid portions may be linked to a central linking group by reacting the carboxylic acid group of the amino acid (a) with an alcohol of an organic group via an esterification reaction, (b) with an amine of an organic group via an amidation reaction, or (c) with a thiol group of an organic group via a thioesterification reaction. Such reactions can result in ester, amide, or thioester linking groups, respectively. Such linking groups, each of which is a type of carbonyl-containing moiety group, may be preferred compared to others for ease of reaction. Compounds formed with such carbonyl-containing moieties may even be preferred for environmental reasons, as these types of groups may break (e.g., hydrolyze) over time and/or in the presence of water, leaving the material to revert, for example, to a common amino acid.

In portions of the central linking group where a heteroatom is not bonded to an amino acid portion, the heteroatom may be capped by a hydrogen.

The central linking group may comprise from 3 to 18 carbon atoms, or from 3 to 16 carbon atoms, preferably from 5 to 12 carbon atoms, more preferably 8 to 12 carbon atoms. Without wishing to be bound by theory, it is believed that a certain minimum of carbon atoms is useful for increasing the relative hydrophobicity of the linking group, and thus the resulting compound, which in turn can help to facilitate increased deposition or performance. It may be preferred that the central linking group further comprises oxygen atoms, for example in such an orientation that the mixture of carbon and oxygen atoms form at least one alkoxylate group, preferably at least one ethoxylate group, at least one propoxylate group, or a mixture thereof.

The modified amino acid multimer compound may comprises a polymeric component of three or more repeating units, for example where the repeating units are alkoxylate groups, preferably ethoxylate groups, propoxylate groups, or a mixture thereof. The central linking group may preferably comprise the polymeric component.

The central linking group may be a divalent, trivalent, tetravalent, pentavalent, or hexavalent organic moiety. The valency typically corresponds to the number of heteroatoms in the central linking group available to react with amino acid portions. The central linking group is preferably a divalent, trivalent, or tetravalent organic moiety, more preferably a divalent moiety. Somewhat lower valency of the central linking group may be preferred to balance loading efficiency of the amino acid portions (and the benefit agent residues that may be present on them) with bulkiness of the resulting compound.

The central linking group may be derived from any suitable organic moiety, preferably one that contains a plurality of heteroatoms. Suitable starting materials for preparing the modified amino acid multimer compounds of the present disclosure preferably contain sufficient heteroatoms selected from O, S, and N, preferably O and N, most preferably O, to enable formation of up to t E groups, where t and E are described in more detail below. Suitable starting materials may be selected from materials that conform to the following structure: $L[GH]_t$, wherein each G is a heteroatom or heteroatom containing moiety independently selected from O, S, NH, and $NR^3$ where $R^3$ is a monovalent moiety with a molecular weight between 14 and 881 Da, preferably between 41 and 255 Da, and where L is as described below.

A variety of simple starting materials may be used to prepare the central linking group of the modified amino acid multimer compounds of the present disclosure. For example, the central linking group may be derived from polyhydric alcohols, polyamines, polythiols, as well as compounds having mixtures of alcohol, thiol, and amine groups, provided the starting materials conform to the restrictions on the number of carbons and heteroatoms described above. The heteroatoms or heteroatom containing moieties in such starting materials may be acylated under conditions well known in the art to arrive at the modified amino acid multimer compounds of the present invention. Any of the materials listed below that are not specifically stated as being either racemic, in an optically pure, or optically enriched state can be in such a state and may serve as suitable starting materials. As described in more detail below, the letter "G" is used herein to describe the heteroatoms to which the amino acid portions may link.

The central linking group may be derived from polyhydric alcohols having two-OH moieties. Suitable polyhydric alcohols with two-OH moieties (each G is O) include, but are not limited to: 1,6-hexanediol; 1,8-octanediol; 1,10-decanediol; 1,12-dodecanediol; 1,2-Ethanediol; 1,2-Propanediol; 1,3-Butanediol; 1,5-Pentanediol; 1,3-Propanediol; 1,7-Heptanediol; 1,9-Nonanediol; 1,11-Undecanediol; 2,3-Butanediol; 2,4-Pentanediol; 2,5-Hexanediol; 1,4-Butanediol; 1,4-Pentanediol; 1,5-Hexanediol; 1,9-Decanediol; 1,7-Octanediol; 1,6-Heptanediol; 1,10-Undecanediol; 1,8-Nonanediol; 2,7-Octanediol; 2,6-Heptanediol; 1,11-Dodecanediol; 2,9-Decanediol; 2,11-Dodecanediol; 2,8-Nonanediol; 2,10-Undecanediol; 1,12-Tridecanediol; 2,12-Tridecanediol; 2,13-Tetradecanediol; Tricyclo[3.3.1.13,7]decane-1,3-diol; 1,2-Benzenediol; 1,2-Propanediol, 3-(2-methoxyphenoxy)-; 1,1-Cyclopropanedimethanol; 1,3-Propanediol, 2-phenyl-; 1,2-Benzenedimethanol; Tricyclo[3.3.1.13,7]decane-1-methanol, 3-hydroxy-; 1,2-Propanediol, 3-(phenylmethoxy)-; 1,3-Propanediol, 2,2-dimethyl-; 1,4-Cyclohexanediol; 1,4-Cyclohexanedimethanol; 1,2-Propanediol, 3-methoxy-; 1,2-Ethanediol, 1-phenyl-; 1,3-Cyclopentanediol; 1,3-Propanediol, 2-(phenylmethoxy)-; [1,1'-Bicyclohexyl]-4,4'-diol; 1,5-Pentanediol, 3-methyl-; Hexitol, 2,5-anhydro-3,4-dideoxy-; Cyclohexanol, 4,4'-(1-methylethylidene)bis-; 1,2-Cyclohexanediol; 1,3-Cyclohexanediol; Cyclohexanemethanol, 4-hydroxy-; 1,3-Propanediol, 2-butyl-2-ethyl-; 1,3-Propanediol, 2-methyl-2-propyl-; 1,3-Propanediol, 2-propyl-; Bicyclo[2.2.2]octane-1,4-dimethanol; 1,3-Dioxolane-2,2-diethanol; 1,2-Propanediol, 3-[(2-ethylhexyl)oxy]-; 1,3-Propanediol, 2-ethyl-2-methyl-; 1,2-Propanediol, 3-phenoxy-; 1,3-Propanediol, 2-pentyl-; 1,3-Pentanediol, 2,2,4-trimethyl-; 1,3-Propanediol, 2-methyl-; Tricyclo[3.3.1.13,7]decane-1,3-dimethanol; 1,3-Hexanediol, 2-ethyl-; 1,2-Propanediol, 3,3-diethoxy-; 1,3-Propanediol, 2-ethyl-; 1,2-Propanediol, 3-(2-propen-1-yloxy)-; 1,1-Cyclopentanedimethanol; [1,1'-Biphenyl]-2,2'-dimethanol; 1,3-Propanediol, 2-butyl-; 1,2-Propanediol, 3-ethoxy-; 1,2-Cyclopentanediol; 1H-Indene-1,2-diol, 2,3-dihydro-; 1,3-Propanediol, 2,2-dibutyl-; 1,2-Benzenediol, 3,6-dimethyl-; 1,5-Pentanediol, 3,3-dimethyl-; 1,2-Benzenediol, 4-octyl-; 1,2-Ethanediol, 1,2-diphenyl-; 1,5-Pentanediol, 2,4-diethyl-; 1,2-Propanediol, 3-(dodecyloxy)-; 1,3-Propanediol, 2-(1-methylethyl)-; 1,2-Propanediol, 3-propoxy-; Cyclohexanemethanol, 2-hydroxy-; 1,4-Butanediol, 2-methyl-; 1,2-Propanediol, 3-(hexyloxy)-; 1,4-Butanediol, 2,2-dimethyl-; 7-Octene-1,2-diol; 1,3-Pentanediol, 2-methyl-; 1,5-Pentanediol, 2 -methyl-; 2,4-Pentanediol, 3-methyl-; 1,2-Propanediol, 3-(nonyloxy)-; 1,3-Cyclohexanedimethanol; 1,3-Butanediol, 2-methyl-; Cyclopentaneethanol, 2-hydroxy-; Tricyclo[3.3.1.13,7]decane-2,4-diol; and 1,5-Hexanediol, 2-ethyl-. Preferred diol materials include: 1,6-hexanediol; 1,8-octanediol; 1,10-decanediol; and 1,12-dodecanediol.

The central linking group may be derived from polyhydric alcohols having three-OH moieties. Suitable polyhydric alcohols with three-OH moieties (each G is O) include, but are not limited to: 1,2,3-Propanetriol (aka, glycerol); 1,2,6-Hexanetriol; 1,2,4-Butanetriol; 1,2,5-Pentanetriol; 1,2,10-Decanetriol; 1,2,8-Octanetriol; 1,2,7-Heptanetriol; 1,2,9-Nonanetriol; 1,3,5-Pentanetriol; 1,4,7-Heptanetriol; 1,3,6-Hexanetriol; 1,3,8-Octanetriol; 1,2,11-Undecanetriol; 1,5,9-Nonanetriol; 1,4,8-Octanetriol; 1,3,10-Decanetriol; 1,4,9-Nonanetriol; 1,4,12-Dodecanetriol; 1,3-Propanediol, 2-ethyl-2-(hydroxymethyl)-; 1,3-Propanediol, 2-(hydroxymethyl)-2-methyl-; 1,3-Propanediol, 2-(hydroxymethyl)-; 1,3-Propanediol, 2-(hydroxymethyl)-2-[(2-propen-1-yloxy)methyl]-; 1,3-Propanediol, 2-(hydroxymethyl)-2-(methoxymethyl)-; 2,4-Pentanediol, 3-ethyl-3-(1-hydroxyethyl)-; 1,3-Propanediol, 2-(hydroxymethyl)-2-propyl-; 2,4-Pentanediol, 3-(hydroxymethyl)-; 1,3-Butanediol, 2-(hydroxymethyl)-3-methyl-; 1,3-Pentanediol, 2-(hydroxymethyl)-2-methyl-; 1,3-Propanediol, 1-(dimethylamino)-2-(hydroxymethyl)-; 1,3-Propanediol, 2-(hydroxymethyl)-2-(phenylmethyl)-; 1,3-Propanediol, 2-(hydroxymethyl)-2-(phenoxymethyl)-; 1,3-Propanediol, 2-(hydroxymethyl)-2-[(2-methylphenoxy)methyl]-; 1,3-Propanediol, 2-(hydroxymethyl)-2-[(2-methoxyphenoxy) methyl]-; Xylopyranoside, methyl 3-deoxy-3-(hydroxymethyl)-, β-D-; Bicyclo[2.2.1]heptane-2,6,7-triol; 1,3-Butanediol, 2-(hydroxymethyl)-; 1,3-Propanediol, 2-hexyl-2-(hydroxymethyl)-; 1,3-; Propanediol, 2-(hydroxymethyl)-2-(3-methylbutyl)-; 1,3-Propanediol, 2-(3-buten-1-yl)-2-(hydroxymethyl)-; 1,3-Propanediol, 2-(hydroxymethyl)-2-[(phenylmethoxy)methyl]-; 1,3-Propanediol, 2-(hydroxymethyl)-2-[(3-methylphenoxy)methyl]-; 1,3-Butanediol, 2-(hydroxymethyl)-2-methyl-; 1,3-Butanediol, 2-ethyl-2-(hydroxymethyl)-; 1,3-Pentanediol, 2-(hydroxymethyl)-4-methyl-; 1,3-Propanediol, 2-(hydroxymethyl)-2-(2-methylpropyl)-; Butanenitrile, 4-hydroxy-3,3-bis(hydroxymethyl)-; 1,3-Propanediol, 2-(hydroxymethyl)-2-[(methoxymethoxy)methyl]-; 1,1-Cyclohexanedimethanol, 2-hydroxy-3-methyl-; 1,3-Cyclopentanediol, 2-(hydroxymethyl)-2-methyl-, (1S,3S)-; 1,3-Propanediol, 2-butyl-2-(hydroxymethyl)-; 1,3-Propanediol, 2-(hydroxymethyl)-2-pentyl-; 2,4-Pentanediol, 3-ethyl-3-(hydroxymethyl)-; 1,3-Propanediol, 2-(ethoxymethyl)-2-(hydroxymethyl)-; 1,3-Butanediol, 2-(hydroxymethyl)-2,3-dimethyl-; 1,3-Butanediol, 2-(hydroxymethyl)-4-methoxy-2-methyl-; 1,3-Propanediol, 2-(hydroxymethyl)-2-octyl-; 1,3-Propanediol, 2-(hydroxymethyl)-2-(2-propen-1 -yl)-; 1,3-Propanediol, 2-(butoxymethyl)-2-(hydroxymethyl)-; 1,3-Propanediol, 2-(propoxymethyl)-2-(hydroxymethyl)-; 4-Pentene-1,3-diol, 2-(hydroxymethyl)-2-methyl-; Butanenitrile, 2,4-dihydroxy-3-(hydroxymethyl)-3-methyl-; 1,3-Propanediol, 2-(hydroxymethyl)-2-[(2-methylbutoxy)methyl]-; Pentanenitrile, 3,5-dihydroxy-4-(hydroxymethyl)-4-methyl-; 1,3-Propanediol, 2-(hydroxymethyl)-1-phenyl-; 1,3-Propanediol, 1-cyclopropyl-2-(hydroxymethyl)-2-methyl-; 1,3-Propanediol, 2-(1-hydroxycyclopropyl)-2-methyl-; 1,3-Propanediol, 1-cyclobutyl-2-(hydroxymethyl)-2-methyl-; 1,3-Cyclopentanediol, 2-(hydroxymethyl)-; 1,3-Cyclopentanediol, 2-(hydroxymethyl)-2-methyl-; 1,3-Cyclohexanediol, 2-(hydroxymethyl)-2-methyl-; 1,1-Cyclopentanedimethanol, 2-hydroxy-4-methoxy-; 1,3-Cyclopentanediol, 2-(hydroxymethyl)-2-(2-propen-1-yl)-; 1,3-Hexanediol, 2-(hydroxymethyl)-4-methyl-; 1,3-Butanediol, 2-(hydroxymethyl)-2-propyl-; 1,3-Butanediol, 2-ethyl-2-(hydroxymethyl)-3-methyl-; 1,3-Pentanediol, 2-(hydroxymethyl)-2,4-dimethyl-; 1,3-Pentanediol, 2-(hydroxymethyl)-4,4-dimethyl-; and 3,5-Heptanediol, 4-(1-hydroxypropyl)-. A preferred triol material is 1,2,3-Propanetriol (aka, glycerol).

The central linking group may be derived from polyhydric alcohols having four-OH moieties. Suitable polyhydric alcohols with four-OH moieties (each G is O) include, but are not limited to: 1,2,3,4-Butanetetrol; 1,2,7,8-Octanetetrol; Hexitol, 3,4-dideoxy-; Hexitol, 2,5-dideoxy-; 1,2,9,10-Decanetetrol; 1,2,6,7-Heptanetetrol; L-threo-Hexitol, 3,4-dideoxy-; D-threo-Hexitol, 2,5-dideoxy-; 1,2,11,12-Dodecanetetrol; D-erythro-Pentitol, 2-deoxy-; Pentitol, 3-deoxy-; erythro-Pentitol, 2-deoxy-; Pentitol, 2-deoxy-; D-threo-Pentitol, 2-deoxy-; 1,4,5,8-Octanetetrol; Hexitol, 2,3-dideoxy-; threo-Hexitol, 3,4-dideoxy-; D-erythro-Hexitol, 2,3-dideoxy-; threo-Hexitol, 2,5-dideoxy-; L-threo-Pentitol, 3-deoxy-; L-threo-Pentitol, 2-deoxy-; Ribitol, 3-deoxy-, D-; 1,2,8,9-Nonanetetrol; 1,3,6,8-Octanetetrol; D-threo-Hexitol, 3,4-dideoxy-; 1,2,5,7-Heptanetetrol; erythro-Pentitol, 3-deoxy-; D-threo-Pentitol, 3-deoxy-; threo-Pentitol, 3-deoxy-; 1,2,4,5-pentanetetrol; 1,3-Propanediol, 2,2-bis(hydroxymethyl)-; 1,2,3-Propanetriol, 2-(hydroxymethyl)-; 1,3-Propanediol, 2-(hydroxymethyl)-2-[[[5-(hydroxymethyl)-1,3-dioxan-5-yl]methoxy]methyl]-; 1,2,4-Cyclopentanetriol, 3-(hydroxymethyl)-5-methoxy-; 1,3-Propanediol, 2-[(hydroxymethoxy)methyl]-2-(hydroxymethyl)-; 1,3-Butanediol, 2,2-bis(hydroxymethyl)-; 1,2,3-Butanetriol, 2-(hydroxymethyl)-; 1,3-Propanediol, 2-(hydroxymethyl)-2-(mercaptomethyl)-; 1,4-Butanediol, 2,2-bis(hydroxymethyl)-; 1,2,4-Butanetriol, 3-(hydroxymethyl)-3-methyl-; 1,3-Propanediol, 2-[[3-(1,1-dimethylethoxy)-2-hydroxypropoxy]methyl]-2-(hydroxymethyl)-; 1,1-Cyclohexanedimethanol, 2,4-dihydroxy-; 1,2,4-Cyclopentanetriol, 3-(hydroxymethyl)-; 1,1,3-Cyclohexanetrimethanol, 2-hydroxy-3-methyl-; 1,2-Cyclobutanedimethanol, 1,3-dihydroxy-; 3aH-Indene-1,2,3a,7-tetrol, octahydro-; 1,1,3-Propanetriol, 2-(hydroxymethyl)-; and 3-Propanediol, and 2-[(2-hydroxyethoxy)methyl]-2-(hydroxymethyl)-. A preferred material with four OH groups is pentaerythritol.

The central linking group may be derived from polyhydric alcohols having five-OH moieties. Suitable polyhydric alcohols with five-OH moieties (each G is O) include, but are not limited to Xylitol; Ribitol; D-Arabinitol; L-Arabinitol; Arabinitol; Pentitol; D-arabino-Hexitol, 5-deoxy-; Hexitol, 3-deoxy-; D-arabino-Hexitol, 2-deoxy-; D-ribo-Hexitol, 2-deoxy-; D-xylo-Hexitol, 5-deoxy-; arabino-Hexitol, 3-deoxy-; xylo-Hexitol, 3-deoxy-; ribo-Hexitol, 3-deoxy-; 1,3,4,5,7-Heptanepentol; 1,2,5,8,9-Nonanepentol; Hexitol, 2-deoxy-; L-arabino-Hexitol, 2-deoxy-; D-xylo-Hexitol, 2-deoxy-; L-arabino-Hexitol, 5-deoxy-; D-erythro-Hexitol, 3-deoxy-, (2ξ)-; 1,2,3,5,7-heptanepentol; 1,1,3,3-Cyclohexanetetramethanol, 2-hydroxy-; 2H-Pyran-3,3,5,5 (4H, 6H)-tetramethanol, 4-hydroxy-; 1,2-Propanediol, 3-[3-hydroxy-2,2-bis(hydroxymethyl)propoxy]-; β-D-erythro-2-Pentulofuranose, 3-C-(hydroxymethyl)-; 1,2,3,4-Butanetetrol, 2-(hydroxymethyl)-; D-Ribofuranose, 2-C-(hydroxymethyl)-; Bicyclo[2.2.1]heptane-2,3,5,6,7-pentol; 1,1,3,3-Cyclopentanetetramethanol, 2-hydroxy-; 1,1,3,3-Cyclohexanetetramethanol, 2-hydroxy-5-methyl-; β-D-Ribopyranose, 2-C-(hydroxymethyl)-; β-D-Lyxopyranose, 2-C-(hydroxymethyl)-; β-D-Ribopyranose, 3-C-(hydroxymethyl)-; α-L-Lyxopyranose, 3-C-(hydroxymethyl)-; β-D-Xylopyranose, 3-C-(hydroxymethyl)-; 5-Cyclohexene-1,2,3,4-tetrol, 2-(hydroxymethyl)-; and 2-Pentulofuranose, 3-C-(hydroxymethyl)-.

The central linking group may be derived from polyhydric alcohols having six-OH moieties. Suitable polyhydric alcohols with six-OH moieties (each G is O) include, but are not limited to D-Mannitol; D-Glucitol; Galactitol; L-Glucitol; L-Iditol; L-Mannitol; Allitol; D-Iditol; L-Altritol; D-Altritol; Mannitol; Hexitol; D-Galactitol; Iditol; Glucitol; Altritol; 1,2,3,5,6,7-heptanehexitol; 1,3-Propanediol, 2,2'-[oxybis(methylene)]bis[2-(hydroxymethyl)-; 1,3-Propanediol, 2,2'-[methylenebis(oxymethylene)]bis[2-(hydroxymethyl)-; 1,5-Pentanediol, 2,2,4,4-tetrakis(hydroxymethyl)-; Pentitol, 3-C-(hydroxymethyl)-; Pentitol, 2-C-(hydroxymethyl)-; D-myo-Inositol, 3-deoxy-3-(hydroxymethyl)-; L-chiro-Inositol, 1-deoxy-1-(hydroxymethyl)-; and 1,2,3,4,5-Cyclopentanepentol, 1-(hydroxymethyl)-.

The central linking group may be derived from materials that include both alcohol and amino moieties. Suitable starting materials containing mixtures of alcohol and amino-GH groups include, but are not limited to those with:

(a) one $NH_2$ and one OH moiety, including but not limited to, 4-Amino-1-butanol; 6-Amino-1-hexanol; 3-Amino-1-propanol; 5-Amino-1-pentanol; 1-Amino-2-butanol; 8-Amino-1-octanol; 10-Amino-1-decanol; 12-Amino-1-dodecanol; 7-Amino-1-heptanol; 4-Amino-2-butanol; 1-Amino-2-pentanol; 11-Amino-1-undecanol; 9-Amino-1-nonanol; 5-Amino-2-pentanol; 1-Amino-3-pentanol; 1-Amino-3-hexanol; 1-Amino-2-hexanol; 1-Amino-2-heptanol; 1-Amino-3-heptanol; 1-Amino-2-decanol; 1-Amino-2-octanol; 1-Amino-3-octanol; 6-Amino-3-hexanol; 1-Amino-2-dodecanol; 1-Amino-2-nonanol; 6-Amino-2-hexanol; 1-Amino-2-undecanol; 2-Pentanol, 5-amino-, (R)-; 1-Amino-3-dodecanol; 1-Amino-3-decanol; 8-Amino-2-octanol; 1-Amino-3-nonanol; 4-Octanol, 8-amino-; 1-Amino-4-heptanol;

(b) one $NH_2$ and two OH moieties, including but not limited to, 3-Amino-1,2-propanediol; 4-Amino-1,2-butanediol; 1-Amino-2,3-butanediol; 4-Amino-1,3-butanediol; 5-Amino-1,2-pentanediol; 1-Amino-2,3-hexanediol; 6-Amino-1,2-hexanediol;

(c) one $NH_2$ and three OH moieties, including but not limited to, 4-Amino-1,2,3-butanetriol; 1-Amino-1,2-dideoxy-D-erythro-pentitol; and (d) one $NH_2$ and four OH moieties, including but not limited to, 1-Amino-1-deoxy-D-ribitol; 1-Amino-1-deoxy-D-arabinitol; Ribamine; 1-Amino-1-deoxy-D-xylitol; 5-Amino-5-deoxy-D-arabinitol; 1-Amino-1-deoxy-L-arabinitol;

(e) two $NH_2$ and one OH moieties, including but not limited to, Pentanol, 1,5-diamino-; Butanol, 1,2-diamino-; Propanol, 1,3-diamino-.

The central linking group may be derived from materials that include both thiol and amino moieties. Suitable starting materials containing mixtures of thiol and amino GH groups include, but are not limited to those with:

(a) one $NH_2$ and one SH moiety, including but not limited to, 1-Butanethiol, 4-amino-; 1-Propanethiol, 3-amino-; 2-Propanethiol, 1-amino-; 1-Pentanethiol, 5-amino-; 1-Hexanethiol, 6-amino-; 1-Heptanethiol, 7-amino-; 2-Pentanethiol, 1-amino-; 1-Octanethiol, 8-amino-; 2-Hexanethiol, 1-amino-; 1-Undecanethiol, 11-amino-; 2-Butanethiol, 1-amino-; 1-Dodecanethiol, 12-amino-; 3-Pentanethiol, 1-amino-; 2-Pentanethiol, 5-amino-; 2-Butanethiol, 4-amino-; 2-Undecanethiol, 1-amino-; 2-Octanethiol, 1-amino-; 2-Nonanethiol, 1-amino-; 2-Hexanethiol, 6-amino-; 2-Heptanethiol, 1-amino-; 1-Decanethiol, 10-amino-; and (b) one $NH_2$ and two SH moieties, including but not limited to, 1,2-Propanedithiol, 3-amino-; 1,3-Butanedithiol, 4-amino-; 2,3-Butanedithiol, 1-amino-; and 1,2-Butanedithiol, 4-amino-.

The central linking group may be derived from materials that include multiple amino groups. Suitable starting materials containing multiple amino GH groups include, but are not limited to those with:

(a) two $NH_2$ moieties, including but not limited to, 1,8-Octanediamine; 1,5-Pentanediamine; 1,6-Hexanediamine; 1,10-Decanediamine; 1,4-Butanediamine; 1,7-Heptanediamine; 1,12-Dodecanediamine; 1,3-Propanediamine; 1,11-Undecanediamine; 1,9-Nonanediamine; 1,3-Pentanediamine; 1,2-Pentanediamine; 1,6-Hexanediamine, 2,2,4 (or 2,4,4)-trimethyl-; 1,4-Pentanediamine; 1,2-Butanediamine; 1,5-Hexanediamine; 1,3-Butanediamine; 1,6-Hexanediamine, C,C,C-trimethyl-; 1,2-Nonanediamine; 1,4-Heptanediamine; 1,2-Heptanediamine; 1,2-Decanediamine; 1,4-Hexanediamine; 1,3-Hexanediamine; 1,2-Propanediamine, N-dodecyl-; 1,2-Octanediamine; 1,6-Octanediamine; 1,7-Octanediamine; 1,2-Dodecanediamine; 1,4-Undecanediamine; 1,6-Hexanediamine, bis(2-methylpropyl)-; 1,2-Undecanediamine; 1,4-Decanediamine; 1,4-Octanediamine; 1,4-Nonanediamine; 1,5-

Pentanediamine, methyl-; 1,6-Heptanediamine; 1,7-Nonanediamine; 1,5-Heptanediamine;

(b) three $NH_2$ moieties, including but not limited to, 1,2,3-Propanetriamine; 1,3,5-Pentanetriamine; 1,4,7-Heptanetriamine; 1,3,6-Hexanetriamine; 1,6,11-Undecanetriamine; 1,2,4-Pentanetriamine; 1,2,4-Butanetriamine; 1,2,5-Pentanetriamine; 1,2,7-Heptanetriamine; 1,2,6-Hexanetriamine; 1,3,5-Hexanetriamine;

(c) one $NH_2$ and one NH moiety, including but not limited to, 1,2-Propanediamine, N-octyl-;

(d) two $NH_2$ moieties and either 0, 1, or 2 NH moieties, including but not limited to, 1,2-Ethanediamine; 1,2-Ethanediamine, N1-(2-aminoethyl)-; 1,2-Ethanediamine, and N1,N2-bis(2-aminoethyl)-.

The central linking group may preferably be derived from a polyhydric alcohol, as such starting materials facilitate convenient processing and desirable release profiles. The polyhydric alcohols may preferably be selected from a diol, a triol, or pentaerythritol, even more preferably selected from: 1,6-hexanediol; 1,8-octanediol; 1,10-decanediol; 1,12-dodecanediol; glycerol; or pentaerythritol.

To facilitate deposition efficiency, for example under aqueous treatment conditions such as in an automatic laundry machine, it may be preferred to select a central linking group that is characterized by a certain degree of hydrophobicity. Put another way, the central linking group may be an organic moiety that is relatively hydrophobic, particularly when the valency of the central linking group is relatively low (e.g., two). A relatively greater number of carbon atoms (e.g., 10 or 12 vs. 3 or 4) may contribute to relatively greater hydrophobicity.

As described above, the central linking group may be joined to the amino acid portion by a carbonyl-containing moiety that is selected from an ester moiety, an amide moiety, or a thioester moiety. Such carbonyl-containing moieties may be formed by reacting the carboxylic acid end of the core amino acid with an appropriate functional group (e.g., an alcohol, an amine, or a thiol) of a suitable organic group that will serve as the central linking group.

It may be preferred that the carbonyl-containing moieties that join the central linking group to the amino acid portions are ester moieties (e.g., the heteroatom is oxygen), for example due to the low cost of alcohol precursors or for the advantageous environmental profile of the resulting esters.

It may be preferred that the carbonyl-containing moieties that join the central linking group to the amino acid portions are amide moieties (e.g., the heteroatom is nitrogen). Amide moieties may be preferred for stability reasons, and/or when the benefit agent fragment is a fragment of an anti-microbial agent. In such cases, the compound may an additional organic moiety, which is preferably hydrophobic, attached to the nitrogen atom. Without wishing to be bound by theory, it is believed that an additional hydrophobic moiety, even if relatively small, can contribute to a suitable degree of hydrophobicity and related performance benefits.

The central linking group may be optionally substituted, although it is preferred that such substitutions are selected so as to maintain the hydrophobic character of the organic group. For example, the organic group may comprise relatively hydrophobic substitutions. Additionally or alternatively, the organic group may comprise hydrophilic substitutions, but it is preferred that they are kept to a minimum and/or that the number of chain atoms is selected accordingly to counteract some of the hydrophilicity of the substitution. For clarity, the substitutions discussed in this paragraph are not intended to include heteroatoms of the central linking group that are further bonded to amino acid portions.

The central linking group may be branched or unbranched. The central linking group may include alkyl branches (including cycloalkyls) and/or aryl branches.

Preferably, the central linking group is linear/unbranched. Such moieties may be preferred because of convenient availability, performance profiles, and relatively low environmental impact.

The central linking group may be derived from a mixture of feedstock materials. The feedstock materials may include materials having variable chain lengths. In such cases, the chain lengths described herein for the central linking group are understood to be weight average chain lengths.

Additionally or alternatively, the feedstock materials used to form the central linking group may include some materials that are linear and some materials that are branched. Therefore, when the feedstocks are reacted to form the precursors or multimer compounds of the present disclosure, some materials will include linear multivalent moieties and others will include branched multivalent moieties. Such mixtures are contemplated in the present disclosure.

The multimer compound may comprise a residue of an additional benefit agent, which may ultimately be released from the modified amino acid multimer compound in addition to the one or more benefit agent residues joined to the nitrogen atom(s) of the amino acid portion(s). Such configurations may be preferred for loading efficiency reasons. Such configurations may also be preferred to allow for a variety of benefit agents to be released from the same compound.

For example, the additional benefit agent residue may have a different identity than the benefit agent residue that is joined to the nitrogen of the core. Both residues may be in the same category of benefit agents (e.g., both are derived from perfume raw materials), but they may have different identities. Preferably, the first and second benefit agents include different functional groups. For example, the first benefit agent may comprise an aldehyde or ketone moiety, and the second benefit agent may comprise a functional group that is not an aldehyde or ketone moiety. The second benefit agent may comprise a functional group that is an alcohol, an amine, a thiol, or a combination thereof.

Preferably, the second benefit agent comprises a functional group that is an alcohol group. Such materials may be preferred to provide a broader spectrum of materials released from the multimer compound (e.g., an aldehyde- or ketone-containing benefit agent, in combination with an alcohol-containing benefit agent).

The central linking group may be substituted with a residue of the additional benefit agent. A side group of an amino acid portion may be substituted with a residue of the additional benefit agent.

The additional benefit agent may be a perfume raw material, preferably an alcohol-containing perfume raw material. In such cases, it is preferred that the first benefit agent (e.g., the parent material of the residue attached to the nitrogen atom of the amino acid portion) is also a perfume raw material, which will allow for more efficient perfume delivery and/or a more complex olfactory experience.

For environmental reasons, it may be preferred that the central linking group is derived from a naturally-derived material or feedstock, particularly when the carbon-containing core is derived from a naturally-occurring amino acid. Suitable naturally-derived materials or feedstocks may include natural fats and/or oils.

The modified amino acid multimer compounds of the present disclosure comprise at least two (and typically up to six) amino acid portions covalently connected by a central linking group. The central linking group may be a divalent moiety that is bound to a carbon atom of the carbonyl group of each amino acid portion. Notably, the multimers of the present disclosure do not comprise a peptide bond. Thus, dipeptides, tripeptides, polypeptides, and the like are not within the scope of the present disclosure. Such materials are not preferred because due to the peptide arrangement, nitrogen atoms of each amino acid portion are not available to be loaded with a benefit agent residue. That being said, it is possible for more general amide-type bonds to be present in the multimers of the present disclosure.

As described above, at least one amino acid portion comprises an organic moiety covalently bonded to the nitrogen atom of the amino acid portion, where the organic moiety comprises a benefit agent residue. When the bond(s) that connects the residue to the nitrogen atom is cleaved, for example upon a triggering event, the multimer compound releases a benefit agent, where the benefit agent comprises an aldehyde moiety, a ketone moiety, or a combination thereof. Such benefit agents are described in more detail below.

One or more, preferably each, of the amino acid portions may comprise an organic moiety covalently bonded to the nitrogen atom of the respective amino acid portion. Preferably, the organic moieties bonded to the respective nitrogen atoms comprise benefit agent residues connected by bonds that are capable of cleaving to release a benefit agent. Such configurations (e.g., two to six benefit agent residues on one multimer compound) may be preferred for loading efficiency reasons.

The modified amino acid multimer compounds of the present disclosure may be characterized by a structure according to Formula I:

$$L[E]_t \qquad \text{Formula I.}$$

In Formula I, the L group represents the central linking group, and at least two (and up to six) of the E groups represent the amino acid portions linked to the central linking group by a heteroatom selected from O, N, or S, preferably O. The multimer compounds generally do not comprise a peptide bond. For the sake of clarity, the multimer (including the central linking group) may comprise an amide bond, so long as it is not a peptide bond.

In Formula I, index t is independently an integer from 2 to 6, preferably 2 to 5, more preferably 2 to 4, more preferably 2 to 3, more preferably 2. Index t largely corresponds to the valency of the central linking group (group L; see below).

In Formula I, L is a central linking group that is multivalent and that comprises 3 to 18 carbon atoms.

In Formula I, each E group is independently selected from -GH, -GX (where X is a suitable charge-balancing counterion), or a moiety according to Formula II:

Formula II

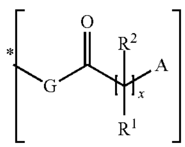

with the proviso that the multimer compound comprises at least two E groups that are moieties according to Formula II. The moieties according to Formula II substantially correspond to the amino acid portions described above. The symbol * indicates the point of attachment of the E group with L.

In Formula II, the value of x is from 1 to 9, preferably from 1 to 6, more preferably from 1 to 3, even more preferably from 1 to 2, even more preferably 1. When x is 1, the moiety according to Formula II (e.g., the amino acid portion) may be derived from a naturally-derived or biosynthesized proteinogenic amino acid, which may be preferred for environmental reasons.

In the moiety according to Formula II, each G (which ultimately corresponds to the heteroatom described above) is independently selected from the group consisting of —O—, —N($R^3$)—, or —S—, preferably wherein each G group is the same. Each $R^3$, if present, is independently selected from H or a monovalent moiety with a molecular weight between 14 and 881 Da, preferably between 41 and 255 Da.

It may be preferred that G is —O—; the resulting ester when G is —O— may be preferred for environmental reasons, as well as convenient availability of alcohol-based feedstock materials that may serve as the central linking group.

It may be preferred that G is —N($R^3$)—. In such cases, relatively smaller $R^3$ moieties, and especially hydrogen, may be preferred when forming the amide bond, for example due to convenient reactions and availability of feedstock materials. Amides can be formed, for example, from protected or unprotected amino acids. When protected, inorganic and organic acids may be most preferred. For unprotected amino acids, chelating catalysts from group III elements, group IV elements, and transition metal catalysts may be preferred; even more preferred are catalysts containing the elements of B, Si, and Ti.

If X is present, X is preferably selected from sodium, potassium, lithium, or ammonium.

In the moiety according to Formula II, each $R^1$ is independently selected from H or a monovalent moiety with a molecular weight between 15 and 507 Da. Preferably $R^1$ is selected from a side group of a proteogenic amino acid or a monovalent moiety with a molecular weight between 15 and 142 Da.

In the moiety according to Formula II, each $R^2$ is independently selected from H and a monovalent moiety with a molecular weight of between 15 and 1000 Da, preferably from 15 to 507 Da, more preferably from 15 to 142 Da. Preferably $R^2$ is H. It may be preferred that at least one $R^2$ comprises a residue of an additional benefit agent, preferably wherein the $R^2$ that comprises the residue is a monovalent moiety with a molecular weight of from 54 and 1000 Da. $R^2$ may comprise at least one residue of a benefit agent. When $R^2$ comprises at least one residue of a benefit agent, $R^2$ is preferably a monovalent moiety with a molecular weight between 54 and 1000 Da. When $R^2$ does not comprise at least one residue of a benefit agent, $R^2$ is preferably selected from H and a monovalent moiety with a molecular weight between 15 and 507 Da, preferably $R^2$ is H or a monovalent moiety with a molecular weight between 15 and 142 Da, more preferably $R^2$ is H.

In the moiety according to Formula II, each A group is a monovalent nitrogen-comprising moiety, wherein at least one A group comprises an independently selected benefit agent residue that is linked to the rest of the A group by one or more bonds, wherein a benefit agent is released when the one or more bonds are cleaved. The benefit agent comprises an aldehyde moiety, a ketone moiety, or a combination thereof.

It may be preferred that each A group is independently selected from the group consisting of: (a) $H_2N$—; (b) ZN—, wherein  represents a linking bond between the nitrogen atom and a carbon atom of the Z group; (c) $HG'(J)_dN(H)$—; and (d)

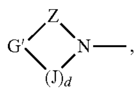

wherein at least one A group is independently selected from (b) or (d), more preferably at least one A group is selected from (b) ZN—, even more preferably both A groups are selected from (b) ZN—, wherein each Z group is an independently selected benefit agent residue. The various moieties (e.g., Z, G', J) and indices (e.g., d) are described in more detail below.

At least one A group may be independently selected to be (b) ZN—, wherein represents a linking bond between the nitrogen atom and a carbon atom of the Z group, wherein the linking bond is one of: (i) a double bond, thereby forming an imine bond, or (ii) a single bond formed from a 1,4-addition when the benefit agent from which the benefit agent residue is derived comprises an alpha-beta unsaturated carbonyl-containing moiety that is an aldehyde moiety or a ketone moiety, wherein the nitrogen atom of the ZN— group is further bonded to a hydrogen (—H).

It may be preferred that in the multimer compound according to Formula I, at least one A group is selected from (b) ZN—, and the Z group of the ZN-moiety is independently selected from the group consisting of

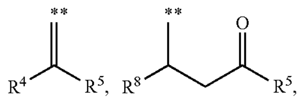

and mixtures thereof, wherein the $=C(R^4)(R^5)$ and $—CH(R^8)CH_2C(O)R^5$ moieties each represent a residue of a benefit agent. The residue of the benefit agent preferably has a molecular formula that differs from the molecular formula of the benefit agent (e.g., from which it is derived and/or that which it becomes when released) only by having one less O atom or one more H atom. The benefit agent comprises an aldehyde moiety, a ketone moiety, or a combination thereof, as such moieties are conveniently reacted with the nitrogen of the amino acid portion.

Preferably, the benefit agent is a perfume raw material comprising from 4 to 34 carbon atoms, preferably wherein $R^4$ is independently selected from a monovalent organic moiety, and wherein $R^5$ and $R^8$ are independently selected from the group consisting of hydrogen and a monovalent organic moiety, with the proviso that $R^4$ and $R^5$, or $R^8$ and $R^5$, may combine to form a cyclic divalent organic moiety. Preferably, $R^5$ and $R^8$ are not both hydrogen in the same Z group. Suitable benefit agents are described in more detail below.

When the ** represents a double bond (e.g., an imine bond), the Z group may be a benefit agent residue having the following structure:

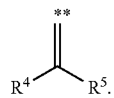

In such cases, $R^4$ may be selected from a monovalent organic moiety, and $R^5$ may be selected from the group consisting of hydrogen and a monovalent organic moiety, with the proviso that $R^4$ and $R^5$ may combine to form a cyclic divalent moiety. When the Z group is a residue of an aldehyde-containing benefit agent, $R^5$ is a hydrogen. When the Z group is a residue t of a ketone-containing benefit agent, $R^5$ is an organic moiety. Such residues may be derived from and/or result in the release of benefit agents according to the formula $R^4—C(O)—R^5$. The benefit agents, and residues thereof, may be characterized by a relatively low molecular weight, for example from about 100 g/mol to about 1000 g/mol, preferably from about 100 g/mol to about 500 g/mol; $R^4$ and $R^5$ groups may be selected accordingly.

When the ** linking bond is a single bond, the Z group may be represented by the following structure:

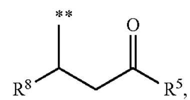

where ** represents the point of attachment of the linking bond to the nitrogen atom (which in this case will also include a hydrogen moiety bonded to the nitrogen, due to the single bond), where $R^5$ and $R^8$ are selected from the group consisting of hydrogen and a monovalent organic moiety. In such cases, the Z group may be derived from an alpha-beta unsaturated carbonyl, such as an aldehyde or ketone. When the Z group is a residue of an aldehyde-containing benefit agent, $R^5$ is a hydrogen. When the Z group is a residue of a ketone-containing benefit agent, $R^5$ is an organic moiety. Preferably, $R^5$ and $R^8$ are not both hydrogen in the same Z group. Such residues may be derived from and/or result in the release of benefit agents according to the formula $R^8—CH{=}CH—C(O)—R^5$.

At least one A group may be independently selected to be (c) $HG'(J)_dN(H)$—, or (d

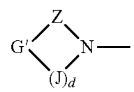

wherein the index d is selected from 1 to 3, preferably d is from 2 to 3, more preferably d is 2; wherein each G' is independently selected from —O—, —S—, or $—N(R^7)—$, preferably wherein G' is —O—, wherein the Z group comprises from 4 to 34 carbon atoms, and wherein the N and the G' are bonded to the same carbon atom of the Z group, wherein each $R^7$, if present, is independently selected from —H or a monovalent moiety with a molecular weight of from about 15 to about 255 Da, preferably wherein $R^7$ is a monovalent moiety with a molecular weight of from about 15 to about 142 Da, more preferably a monovalent moiety with a molecular weight from about 15 to about 30 Da, wherein each J is independently selected from the group consisting of $C(R^9)_2$, —O—, and $—N(R^9)$, preferably each J is $C(R^9)_2$, wherein each $R^9$ is independently selected from H or a monovalent moiety with a molecular weight between 14 and 990 Da, more preferably $R^9$ is selected from H or a monovalent moiety with a molecular weight between 14 and 186 Da, even more preferably $R^9$ is H, with the proviso that a first $R^9$ and a second $R^9$ can optionally be taken together, where feasible, as a divalent substituent, preferably where the divalent substituent is selected from the group consisting of a fused ring, a spirocyclic ring, and an unsaturated substituent selected from $=N(R^7)$, $=O$, and $=S$, wherein $R^7$, if present, is as defined above.

It may be preferred that at least one of the following is true, with a potential benefit of the configuration provided in parenthesis: for a given compound, more than one A group comprises a benefit agent residue (efficient loading); for a given compound, the identity of the A groups are identical (convenient processing); for a given compound, the identity of the A groups are different (allowing for flexible and/or tunable processing); for a given compound, the identity of the Z groups are identical (convenient loading and/or efficient delivery of a particular benefit agent); and/or for a given compound, the identity of the Z groups are different (convenient delivery of multiple benefit agents, allowing for more complex performance benefits). More than one of these statements may be true, so long as not inconsistent.

Benefit Agents and Residues Thereof

The modified amino acid multimer compounds of the present disclosure comprise benefit agent residues that are derived from aldehyde-containing benefit agents, ketone-comprising benefit agents, or a combination thereof. The benefit agent residue may be derived from a benefit agent that comprises an aldehyde moiety. The benefit agent residue may be derived from a benefit agent that comprises a ketone moiety. The benefit agent may comprise an alpha-beta unsaturated carbonyl group that is an aldehyde or ketone moiety.

As used herein, the benefit agent from which the benefit agent residue is derived may be called a parent benefit agent.

The aldehyde or ketone moiety of the parent benefit agent may react with a nitrogen atom of the amino acid portion (e.g., at the N terminus), resulting in a benefit agent fragment being joined to the core at the nitrogen atom. As described above, this may be through a linking bond that may be a double bond that is an imine bond or a single bond formed through a 1,4-addition process, such as a 1,4 Michael-type addition. When the linking bond connecting the benefit agent fragment to the nitrogen atom is formed through a 1,4-addition, the parent benefit agent may comprise an alpha-beta unsaturated carbonyl, where the carbonyl is an aldehyde moiety or a ketone moiety.

When the linking bond is broken, for example through hydrolysis, the benefit agent is released. The linking bond may be broken through a triggering condition, such as the presence of water or increased temperature. When the treatment composition is used to treat fabrics, such triggering conditions may occur during normal usage, such as during wear, storage, or while wiping or toweling off a wet surface. It may be that the linking bond may also be broken under ambient decomposition, e.g. upon the passage of time.

The benefit agent residue may be derived from any suitable benefit agent, which may include a perfume raw material, an antimicrobial agent, a pesticide, an insect repellant, an anti-fungal agent, a herbicidal agent, a hueing dye, an antioxidant, a non-perfume organoleptic, or a combination thereof, preferably a perfume raw material, an antimicrobial agent, or a combination thereof, more preferably a perfume raw material. A few of these benefit agents are discussed in more detail below.

A. Perfume Raw Materials

The benefit agent may be a perfume raw material ("PRM") that comprises an aldehyde moiety, a ketone moiety, or a mixture thereof. The benefit agent residue (e.g., the Z group) may be derived from a perfume raw material.

The term "perfume raw material" (or "PRM") as used herein refers to compounds that may have a molecular weight of at least about 100 g/mol (optionally up to about 1000 g/mol, preferably up to about 500 g/mol) and which are useful in imparting an odor, fragrance, essence, or scent, either alone or with other perfume raw materials. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

Perfume raw materials that comprise an aldehyde moiety are provided below in Table B. It is believed that the materials provided in Table B are illustrative (but non-limiting) examples of PRMs that are suitable for use according to the present disclosure.

TABLE B

Aldehyde-containing perfume raw materials.

| Number | Registry Name | Trade Name |
|---|---|---|
| 1 | 3-Cyclohexene-1-carboxaldehyde, dimethyl- | Ligustral |
| 2 | 3-Cyclohexene-1-carboxaldehyde, 2,4,6-trimethyl- | Isocyclocitral |
| 3 | Cyclohexanemethanol, .alpha., 3,3-trimethyl-, formate | Aphermate |
| 4 | 3-(4-tert-butylphenyl)butanal; pt-bucinal; 3-(4-tert-butylphenyl)butanal | Lilial |
| 5 | 2-methylundecanal | Methyl Nonyl Acetaldehyde |
| 6 | 1-methyl-3-(4-methylpent-3-enyl)cyclohex-3-ene-1-carbaldehyde; myrmac aldehyde | Precyclemone B |
| 7 | Benzenepropanal, 3-(4-ethylphenyl)-2,2-dimethylpropanal | Floralozone |
| 8 | 2,4-dimethylcyclohex-3-ene-1-carbaldehyde | Ligustral/Triplal |
| 9 | Decanal | Decyl Aldehyde |
| 10 | 10-Undecen-1-al; Undecenoic aldehyde; n-Undecenoic aldehyde; Hendecen-10-al; | Undecylenic aldehyde; Aldehyde C-11, unsaturated; Aldehyde C-11 undecylenic; |

TABLE B-continued

| Aldehyde-containing perfume raw materials. | | |
|---|---|---|
| Number | Registry Name | Trade Name |
| 11 | 8-, 9 and 10-Undecenal, mixture of isomers | Intreleven aldehyde |
| 12 | Benzenepropanal, .alpha.-methyl-4-(1-methylethyl)- | Cylamen Aldehyde; |
| 13 | 2,6,10-trimethylundec-9-enal | Adoxal; Farenal |
| 14 | 4-(octahydro-4,7-methano-5H-inden-5-ylidene)butanal | Dupical |
| 15 | 3-Ethoxy-4-hydroxybenzaldehyde | Ethyl vanillin |
| 16 | tricyclo[5.2.1.02,6]decane-3-carbaldehyde | Vertral ® |
| 17 | 4,7-Methano-1H-indene-2-carboxaldehyde, octahydro-5-methoxy-; 6-Methoxy dicyclopentadiene carboxaldehyde; 8-Methoxytricyclo(5.2.2.1)decane-4-carboxaldehyde; Octahydro-5-methoxy-4,7-methano-1H-indene-2-carboxaldehyde; | Scentenal ® 981810 |
| 18 | 4-Hydroxy-3-methoxybenzaldehyde | Vanillin |
| 19 | Trans-4-decenal | Decenal-4-trans |
| 20 | α-hexyl-; α-n-Hexyl-β-phenylcrolein; 2-Hexyl-3-phenyl-2-propenal; 2-Hexyl-3-phenyl-propenal; (2Z)-2-Hexyl-3-phenyl-2-propenal; Hexyl-3-phenyl-propenal; n-Hexyl cinnamaldehyde; (2E)-2-Benzylideneoctanal; 2-[(E)-Benzylidene]octanal | α-Hexylcinnamaldehyde; α-Hexylcinnamic aldehyde; Hexyl cinnamic aldehyde; Hexylcinnamaldehyde; Cinnamaldehyde, |
| 21 | 4-Dodecenal | Tangerinal DIPG 984655 |
| 22 | 3-Cyclohexene-1-propanal,beta,4-dimethyl- | Liminal ® 955374 |
| 23 | trans-2-Dodecenal | Mandarine aldehyde 10% CITR 965765 |
| 24 | 4,8-Dimethyl-4,9-decadienal | Floral Super |
| 25 | Hydroxymyrac aldehyde; 4-(4-Hydroxy-4-methyl-pentyl)-3-cyclohexen-1-carboxyaldehyde; Lyral; Kovanol | Lyral |
| 26 | 2-Hexenal, (E)- | 2-Hexenal |
| 27 | Benzaldehyde | Benzaldehyde |
| 28 | Benzeneacetaldehyde | Phenyl Acetaldehyde |
| 29 | Benzeneacetaldehyde, .alpha.-methyl- | Hydratropic Aldehyde |
| 30 | 3-Cyclohexene-1-carboxaldehyde, 3,5-dimethyl- | Cyclal C, |
| 31 | Benzaldehyde, 4-methoxy- | Anisic Aldehyde |
| 32 | Octanal, 7-hydroxy-3,7-dimethyl- | Hydroxycitronellal |
| 33 | 3-Cyclohexene-1-carboxaldehyde, 3,6-dimethyl- | Cyclovertal |
| 34 | Octanal, 7-methoxy-3,7-dimethyl- | Methoxycitronellal Pq |
| 35 | Benzenepropanal, beta.-methyl-; 3-phenylbutanal | Trifernal |
| 36 | 4,7-Methano-1H-indenecarboxaldehyde, octahydro- | Formyltricyclodecan |
| 37 | Octanal | Octyl Aldehyde |
| 38 | 5-Heptenal, 2,6-dimethyl- | Melonal |
| 39 | Octanal, 3,7-dimethyl- | Dihydrocitronellal |
| 40 | 2-Nonenal | 2 Nonen-1-al |
| 41 | 6-Octenal, 3,7-dimethyl- | Citronellal |
| 42 | 2-Decenal | 2 Decene-1-al |
| 43 | 2,6-Octadienal, 3,7-dimethyl- | Citral |
| 44 | Undecenal | Iso C-11 Aldehyde |
| 45 | Undecanal | Undecyl Aldehyde |
| 46 | 2-Undecenal | 2-Undecene-1-Al |
| 47 | Benzaldehyde, 4-(1-methylethyl)- | Cuminic Aldehyde |
| 48 | Decanal, 2-methyl- | Methyl Octyl Acetaldehyde |
| 49 | Benzenepropanal, 4-(1,1-dimethylethyl)- | Bourgeonal |
| 50 | 2-Dodecenal | 2 Dodecene-1-al |
| 51 | Benzenepropanal, .beta.-methyl-3-(1-methylethyl)- | Florhydral |
| 52 | 1,3-Benzodioxole-5-carboxaldehyde | Heliotropin |
| 53 | 3-Cyclohexene-1-carboxaldehyde, 1-methyl-4-(4-methylpentyl)- | Vernaldehyde |
| 54 | Benzenepropanal, 4-methoxy-.alpha.-methyl- | Canthoxal |
| 55 | Cyclohexenebutanal, .alpha.,2.2.6-tetramethyl- | Cetonal |
| 56 | Dodecanal | Lauric Aldehyde |
| 57 | 5,9-Undecadienal, 2,6,10-trimethyl- | Oncidal |
| 58 | Bicyclo[2.2.2]oct-5-ene-2-carboxaldehyde, 6-methyl-8-(1-methylethyl)- | Maceal |
| 59 | 2-methyl-3-[4-(2-methylpropyl)phenyl]propanal | cyclamen homoaldehyde |

TABLE B-continued

| Aldehyde-containing perfume raw materials. | | |
|---|---|---|
| Number | Registry Name | Trade Name |
| 60 | 6-methoxy-2,6-dimethyloctanal | calypsone |
| 61 | 4-propan-2-ylbenzaldehyde | Cuminic Aldehyde |
| 62 | 3,6-dimethylcyclohex-3-ene-1-carbaldehyde | VERTOLIFF |
| 63 | 2-methyl-3-(4-methylphenyl)propanal | Jasmorange ®; satinaldehyde |
| 64 | 3-phenylprop-2-enal | Cinnamic Aldehyde |

The perfume raw material that formed the benefit agent residue may be selected from the group consisting of the aldehyde-containing PRMs of Table B, above. The PRM that formed the PRM residue may comprise an aldehyde moiety and preferably be selected from the group consisting of: methyl nonyl acetaldehyde: benzaldehyde; floralozone; isocyclocitral; triplal (ligustral); precylcemone B; lilial; decyl aldehyde; undecylenic aldehyde; cyclamen homoaldehyde; cyclamen aldehyde; dupical; oncidal; adoxal; melonal; calypsone; anisic aldehyde; heliotropin; cuminic aldehyde; scentenal; 3,6-dimethylcyclohex-3-ene-1-carbaldehyde; satinaldehyde; canthoxal; vanillin; ethyl vanillin; cinnamic aldehyde; cis-4-decenal; trans-4-decenal; cis-7-decenal; undecylenic aldehyde; trans-2-hexenal; trans-2-octenal; 2-undecenal; 2,4-dodecadeienal; cis-4-heptenal; Florydral; butyl cinnamaldehyde; limonelal; amyl cinnamaldehyde; hexyl cinnamaldehyde; citronellal; citral; cis-3-hexen-1-al; and mixtures thereof.

As mentioned above, the multimer compound may include a residue of a perfume raw material that comprises a ketone moiety. Perfume raw materials that comprise a ketone moiety are provided below in Table C. It is believed that the materials provided in Table Care illustrative (but non-limiting) examples of PRMs that are suitable for use according to the present disclosure.

TABLE C

| Ketone-containing perfume raw materials. | | |
|---|---|---|
| Number | Registry Name | Trade Name |
| 1 | 2-Buten-1-one, 1-(2,6,6-trimethyl-3-cyclohexen-1-yl)- | delta-Damascone |
| 2 | (1-(2,6,6-Trimethyl-2-cyclohexen-1-yl)-2-buten-1-one); 2-Buten-1-one, 1-(2,6,6-trimethyl-2-cyclohexen-1-yl)-, (E)- | alpha-Damascone |
| 3 | (1-(2,6,6-Trimethyl-1-cyclohexen-1-yl)-2-buten-1-one); 2-Buten-1-one, 1-(2,6,6-trimethyl-1-cyclohexen-1-yl)-, (E)- | beta-Damascone |
| 4 | 2-Buten-1-one, 1-(2,6,6-trimethyl-1,3-cyclohexadien-1-yl)- | Damascenone |
| 5 | 1,1,2,3,3-pentamethyl-2,5,6,7-tetrahydroinden-4-one | Cashmeran |
| 6 | 1-(5,5-dimethyl-1-cyclohexenyl)pent-4-en-1-one | Neobutenone Alpha |
| 7 | 1-(5,5-dimethyl-1-cyclohexenyl)pent-4-en-1-one | Galbascone; Dynascone |
| 8 | 1-naphthalen-2-ylethanone | Methyl Beta-Naphthyl Ketone |
| 9 | 2-(2-(4-Methyl-3-cyclohexen-1-yl)propyl)cyclo-pentanone | Nectaryl |
| 10 | 2-Hexyl-2-cyclopenten-1-one (main component) | Isojasmone B 11 |
| 11 | Methyl 2,6,10-Trimethyl-2,5,9-cyclododecatrien-1-yl ketone; | Trimofix "O" |
| 12 | α-Isomethyl ionone; 5-(2,6,6-Trimethyl-2-cyclohexen-1-yl)-3-methyl-3-buten-2-one; | Methyl ionone; Methyl Ionone Alpha Iso; Methyl Ionone Gamma; Isoraldeine 70; Isoraldeine 95; Gamma Methylionone 600 UC; Alpha Daphnone; Iraldeine gamma; gamma Methyl Ionone Pure; gamma Methyl Ionone A; Gamma Methyl Ionone Coeur |
| 13 | 2-Heptylcyclopentanone; | Fleuramone; Projasmon |
| 14 | 3-(Hydroxymethyl)nonan-2-one (and isomer) | Methyl lavender ketone |
| 15 | 2-Cyclohexen-1-one, 2-methyl-5-(1-methylethenyl)-, (R)- | Laevo Carvone |
| 16 | Bicyclo[2.2.1]heptan-2-one, 1,7,7-trimethyl-, (1R)- | Camphor Gum |
| 17 | 2-Heptanone | Methyl Amyl Ketone |
| 18 | 3-Octanone | Ethyl Amyl Ketone |
| 19 | 2-Octanone | Methyl Hexyl Ketone |
| 20 | 5-Hepten-2-one, 6-methyl- | Methyl Heptenone |

TABLE C-continued

| Ketone-containing perfume raw materials. | | |
|---|---|---|
| Number | Registry Name | Trade Name |
| 21 | Ethanone, 1-(4-methylphenyl)- | Para Methyl Acetophenone |
| 22 | 2-Butanone, 4-phenyl- | Benzyl Acetone |
| 23 | 1,4-Methanonaphthalen-5(1H)-one, 4,4a,6,7,8,8a-hexahydro- | Tamisone |
| 24 | 2H-1-Benzopyran-2-one, 3,4-dihydro- | Dihydrocoumarin |
| 25 | Cyclohexanone, 5-methyl-2-(1-methylethyl)-, cis- | Iso Menthone |
| 26 | 2H-Pyran-2-one, 6-butyltetrahydro- | Nonalactone |
| 27 | 3-Hepten-2-one, 3,4,5,6,6-pentamethyl- | Koavone |
| 28 | Cyclopentanone, 3-methyl-2-pentyl- | Jasmylone |
| 29 | 3-Nonanone | Ethyl Hexyl Ketone |
| 30 | Ethanone, 1-(3,3-dimethylcyclohexyl)- | Herbac |
| 31 | 3-Heptanone, 5-methyl-, oxime | Stemone |
| 32 | Cyclohexanone, 2-(1-methylpropyl)- | 2-Sec-Butyl Cyclo Hexanone |
| 33 | Cyclopentanone, 2-pentyl- | Delphone |
| 34 | 2-Cyclopenten-1-one, 3-methyl-2-pentyl- | Dihydrojasmone |
| 35 | Cyclohexanone, 5-methyl-2-(1-methylethyl)-, trans- | Menthone Racemic |
| 36 | Cyclohexanone, 4-(1,1-dimethylpropyl)- | Orivone |
| 37 | 2-Undecanone | Methyl Nonyl Ketone |
| 38 | 1-Decanol | Rhodalione |
| 39 | 2-Cyclohexen-1-one, 3-methyl-5-propyl- | Livescone |
| 40 | 2-Cyclopenten-1-one, 2-methyl-3-(2-pentenyl)- | Iso Jasmone |
| 41 | Ionone | Ionone Ab |
| 42 | 3-Buten-2-one, 4-(2,6,6-trimethyl-2-cyclohexen-1-yl)-, (E)- | Ionone Alpha |
| 43 | 3-Buten-2-one, 4-(2,6,6-trimethyl-1-cyclohexen-1-yl)- | Ionone Beta |
| 44 | 2-Buten-1-one, 1-(2,4,4-trimethyl-2-cyclohexen-1-yl)-, (E)- | Isodamascone N |
| 45 | 2H-1-Benzopyran-2-one | Coumarin |
| 46 | Cyclopentanone, 2-heptyl- | Fleuramone |
| 47 | 3-Decanone, 1-hydroxy- | Methyl Lavender Ketone |
| 48 | 1-Propanone, 1-[2-methyl-5-(1-methylethyl)-2-cyclohexen-1-yl]- | Nerone |
| 49 | 9-Undecen-2-one, 6,10-dimethyl- | Tetra Hydro Psuedo Ionone |
| 50 | 1-phenylethanone | Acetophenone |
| 51 | 2-butan-2-ylcyclohexan-1-one | Freskomenthe |
| 52 | Ethanone, 1-(3-methyl-2-benzofuranyl)- | nerolione |
| 53 | 4-(4-methoxyphenyl)butan-2-one | Anisyl Acetone |

The perfume raw material that formed the benefit agent residue may be selected from the group consisting of the ketone-containing PRMs of Table C, above. The PRM that formed the residue may comprise a ketone moiety and may preferably be selected from the group consisting of: nerolione; 4-(4-methoxyphenyl) butan-2-one; 1-naphthalen-2-ylethanone; nectaryl; trimofix O; fleuramone; delta-damascone; beta-damascone; alpha-damascone; methyl ionone; 2-hexylcyclopent-2-en-1-one; galbascone; and mixtures thereof.

The benefit agent residue may be derived from a benefit agent that is a perfume raw material, preferably a perfume raw material selected from the group consisting of: methyl nonyl acetaldehyde: benzaldehyde; floralozone; isocyclocitral; triplal (ligustral); precylcemone B; lilial; decyl aldehyde; undecylenic aldehyde; cyclamen homoaldehyde; cyclamen aldehyde; dupical; oncidal; adoxal; melonal; calypsone; anisic aldehyde; heliotropin; cuminic aldehyde; scentenal; 3,6-dimethylcyclohex-3-ene-1-carbaldehyde; satinaldehyde; canthoxal; vanillin; ethyl vanillin; cinnamic aldehyde; cis-4-decenal; trans-4-decenal; cis-7-decenal; undecylenic aldehyde; trans-2-hexenal; trans-2-octenal; 2-undecenal; 2,4-dodecadeienal; cis-4-heptenal; Florydral; butyl cinnamaldehyde; limonelal; amyl cinnamaldehyde; hexyl cinnamaldehyde; citronellal; citral; cis-3-hexen-1-al; nerolione; 4-(4-methoxyphenyl) butan-2-one; 1-naphthalen-2-ylethanone; nectaryl; trimofix O; fleuramone; delta-damascone; beta-damascone; alpha-damascone; methyl ionone; 2-hexylcyclopent-2-en-1-one; galbascone; and mixtures thereof. Materials, preferably materials from Tables B and C, may be present as a mixture, as mixtures of PRMs are likely to give preferred scent experiences.

The perfume raw materials in this specification, including the perfume raw materials listed above, can be obtained from various suppliers including: International Flavors and Fragrances of New York, NY USA; Givaudan of Vernier Switzerland; Firmenich of Geneva, Switzerland; Symrise of Holzminden, Germany; Kao of Tokyo, Japan; Takasago of Tokyo, Japan; and Florasynth of Tel-Aviv, Israel.

B. Anti-Microbial Agents

The benefit agent may be an anti-microbial agent that comprises an aldehyde moiety, a ketone moiety, or a mixture thereof. Suitable anti-microbial agents for use in the present multimer compounds may include acetylacetone enolate, gossypol, nootkatone, or mixtures thereof.

Methods of Making a Modified Amino Acid Multimer Compound and Related Precursor Compounds The modified amino acid multimer compounds according to the present disclosure may be made by reacting a multimer precursor compound with a benefit agent. The present disclosure thus relates to processes of making a modified amino acid multimer compound.

The modified amino acid multimer precursor compound (or "multimer precursor compound" or even simply "precursor compound" as used herein) may comprise at least two amino acid portions that are covalently bonded to a central linking group.

For example, the modified amino acid multimer precursor compounds of the present disclosure may comprise a central linking group and from two to six amino acid portions that are each covalently linked to the central linking group by a (separate) heteroatom selected from the group consisting of O, S, and N, preferably O, wherein the central linking group comprises from 3 to 18 carbon atoms, wherein each amino acid portion comprises a carbon backbone comprising one or more carbon atoms, a carbonyl group that comprises a carbon atom, and a nitrogen atom, wherein the heteroatom is directly bonded to the carbon atom of the carbonyl group and to the central linking group.

The precursor compound does not (yet) comprise a residue of a benefit agent connected to a nitrogen atom of any of the amino acid portions. In effect, the precursor compound may be the modified amino acid multimer compound prior to its reaction with the benefit agent, where the nitrogen atom is in primary amine ($—NH_2$) form, or in $HG'(J)_dN(H)$ form. The cores, side groups, carbonyl-containing moieties, and hydrophobic moieties are preferably as previously described.

The modified amino acid multimer precursor compound may have a structure according to Formula I', $$L[E]_t \qquad \text{Formula I'},$$

wherein in L, E, and t are defined as above, with the proviso that the multimer precursor compound comprises at least two E groups that are moieties according to Formula II as defined above, with the further proviso that each A group of the moieties according to Formula II are selected from: (a) $H_2N—$, or (c) $HG'(J)_dN(H)—$, wherein G', J, and d are defined as above. Other than for A, the preferences provided above for the remaining groups or indices equally apply to Formula I'.

A multivalent central linking group may be modified with amino acid portions by reacting a compound according to the following formula $L[GH]_t$ with the carboxyl groups of two or more amino acids, for example through an esterification, an amidation, or a thioesterification reaction.

Thus, the present disclosure relates to a method of making a modified amino acid multimer precursor compound, the method comprising: providing a multivalent central linking group; reacting the central linking group, preferably through the heteroatoms, with two or more (preferably up to six) amino acids, preferably at the carboxylic acid/C terminus.

A modified amino acid multimer precursor compound may be obtained from the following steps: (i) providing t molar equivalent of an amino acid portion comprising a carboxylic acid terminus; (ii) providing one molar equivalent of $L[GH]_t$ to form a mixture; (iii) combining the mixture of amino acid portion and $L[GH]_t$ with a slight molar excess of acid (preferably sulfuric acid, methanesulfonic acid, or para-toluenesulfonic acid, mixtures thereof) into a suitable reaction vessel; (iv) heating the combined mixture between 100° C. and 150° C. for between 1 hour to 36 hours; (v) adjusting the pH to at least about 7; and (vi) separating at least a portion of the salts formed upon neutralization from the product.

The multimer precursor compound (and/or a multimer precursor composition made according to the methods provided herein) may be reacted with a benefit agent to form the modified amino acid multimer compound as described herein.

Adjunct Ingredient

The treatment compositions of the present disclosure, which may be consumer products, may comprise an adjunct material. The adjunct material may provide a benefit in the intended end-use of a composition, or it may be a processing and/or stability aid.

Suitable adjunct materials may include: surfactants, conditioning actives, deposition aids, rheology modifiers or structurants, antioxidants, bleach systems, stabilizers, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, silicones, hueing agents, aesthetic dyes, neat perfume, perfume delivery systems (such as core/shell encapsulates, other pro-fragrance materials, and the like), structure elasticizing agents, carriers, hydrotropes, processing aids, anti-agglomeration agents, coatings, formaldehyde scavengers, and/or pigments.

Depending on the intended form, formulation, and/or end-use, compositions of the present disclosure or may not may not contain one or more of the following adjunct materials: surfactants, conditioning actives, deposition aids, rheology modifiers or structurants, antioxidants, bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments.

The precise nature of these additional components, and levels of incorporation thereof, will depend on the physical form of the composition and the nature of the operation for which it is to be used. However, when one or more adjuncts are present, such one or more adjuncts may be present as detailed below. The following is a non-limiting list of suitable additional adjuncts.

A. Surfactants

The treatment compositions of the present disclosure may comprise surfactant. Surfactants may be useful for providing, for example, cleaning benefits. The compositions may comprise a surfactant system, which may contain one or more surfactants.

The treatment compositions of the present disclosure may include from about 0.1% to about 70%, or from about 2% to about 60%, or from about 5% to about 50%, by weight of the composition, of a surfactant system. Liquid compositions may include from about 5% to about 40%, by weight of the composition, of a surfactant system. Compact formulations, including compact liquids, gels, and/or compositions suitable for a unit dose form, may include from about 25% to about 70%, or from about 30% to about 50%, by weight of the composition, of a surfactant system.

The surfactant system may include anionic surfactant, nonionic surfactant, zwitterionic surfactant, cationic surfactant, amphoteric surfactant, or combinations thereof. The surfactant system may include linear alkyl benzene sulfonate, alkyl ethoxylated sulfate, alkyl sulfate, nonionic surfactant such as ethoxylated alcohol, amine oxide, or mixtures thereof. The surfactants may be, at least in part, derived from natural sources, such as natural feedstock alcohols.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES), alkyl sulfates (AS), or mixtures thereof. Other suitable anionic surfactants include branched modified alkyl benzene sulfonates (MLAS), methyl ester sulfonates (MES), sodium lauryl sulfate (SLS), sodium lauryl ether sulfate (SLES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine).

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branhed alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as $C_{12}$-$C_{14}$ EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12-14}$ dimethyl amine oxide), and/or sulfo and hydroxy betaines, such as N-alkyl-N,N-dimethylammino-1-propane sulfonate where the alkyl group can be $C_8$ to $C_{18}$, or from $C_{10}$ to $C_{14}$. The zwitterionic surfactant may include amine oxide.

Depending on the formulation and/or the intended end-use, the composition may be substantially free of certain surfactants. For example, liquid fabric enhancer compositions, such as fabric softeners, may be substantially free of anionic surfactant, as such surfactants may negatively interact with cationic ingredients.

B. Conditioning Active

The treatment compositions of the present disclosure may include a conditioning active. Compositions that contain conditioning actives may provide softness, anti-wrinkle, anti-static, conditioning, anti-stretch, color, and/or appearance benefits.

Conditioning actives may be present at a level of from about 1% to about 99%, by weight of the composition. The composition may include from about 1%, or from about 2%, or from about 3%, to about 99%, or to about 75%, or to about 50%, or to about 40%, or to about 35%, or to about 30%, or to about 25%, or to about 20%, or to about 15%, or to about 10%, by weight of the composition, of conditioning active. The composition may include from about 5% to about 30%, by weight of the composition, of conditioning active.

Conditioning actives suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, polyhydroxystearic acid and/or derivatives thereof, glyceride copolymers, or combinations thereof. Preferably, the conditioning active is a cationic conditioning active, which may improve the delivery/deposition of the multimer compound.

The treatment composition may comprise a conditioning active, where the conditioning active comprises quaternary ammonium ester compounds. Preferably, the quaternary ammonium ester compounds are present at a level of from about 2 wt % to about 35 wt %, preferably from about 4 wt % to about 25 wt %, more 5 wt % to about 20 wt %, even more preferably from about 6 wt % to about 15 wt %, even more preferably from about 7 wt % to about 12 wt %, by weight of the treatment composition. The quaternary ammonium ester compounds (also known as "ester quats") may be monoester quats, diester quats, triester quats, or a combination thereof; preferably, diester quat material forms the major portion (whether a majority or a plurality) of the ester quat compounds. It is believed that in addition to providing conditioning benefits, selecting the proper type and/or level of conditioning active (namely, a quaternary ammonium ester compound) can improve the deposition and/or performance of the multimer compounds described in the present disclosure.

The quaternary ammonium ester compound may comprise compounds according to the following formula:

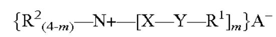

$$\{R^2_{(4-m)}—N+—[X—Y—R^1]_m\}A^-$$

wherein:

m is 1, 2 or 3, with provisos that, in a given molecule, the value of each m is identical;

each $R^1$, which may comprise from 13 to 22 carbon atoms, is independently a linear hydrocarbyl or branched hydrocarbyl group, preferably $R^1$ is linear, more preferably $R^1$ is partially unsaturated linear alkyl chain;

each $R^2$ is independently a $C_1$-$C_3$ alkyl or hydroxyalkyl group and/or each $R^2$ is selected from methyl, ethyl, propyl, hydroxyethyl, 2-hydroxypropyl, 1-methyl-2-hydroxyethyl, poly($C_2$-$C_3$ alkoxy), polyethoxy, benzyl, more preferably methyl or hydroxyethyl;

each X is independently $—(CH_2)_n—$, $—CH_2—CH(CH_3)—$ or $—CH(CH_3)—CH_2—$, where each n is independently 1, 2, 3 or 4, preferably each n is 2;

each Y is independently —O—(O)C— or —C(O)—O—; and

A− is independently selected from the group consisting of chloride, bromide, methyl sulfate, ethyl sulfate, sulfate, and nitrate, preferably A− is selected from the group consisting of chloride and methyl sulfate, more preferably A− is methyl sulfate.

For monoester quats, m is 1. For diester quats, m is 2. For triester quats, m is 3. The conditioning active may comprise a mixture of monoester quats and diester quats, or even a mixture of monoester quats, diester quats, and triester quats. As will be appreciated by one of ordinary skill, the mixture may depend, in part, on the starting/feedstock materials, such dialkanolamines or trialkanolamines.

The quaternary ammonium ester compound may be derived from fatty acids characterized by an Iodine Value of from 0 to 140, or from 0 to about 90, or from about 10 to about 70, or from about 15 to about 50, or from about 18 to about 30. Iodine Values may be determined according to the method provided in US2020/0407665 (equivalent to WO2020/264566).

The composition may include a quaternary ammonium ester compound, a silicone, or combinations thereof, preferably a combination. The combined total amount of quaternary ammonium ester compound and silicone may be from about 5% to about 70%, or from about 6% to about 50%, or from about 7% to about 40%, or from about 10% to about 30%, or from about 15% to about 25%, by weight of the composition. The composition may include a quaternary ammonium ester compound and silicone in a weight ratio of from about 1:10 to about 10:1, or from about 1:5 to about 5:1, or from about 1:3 to about 1:3, or from about 1:2 to about 2:1, or about 1:1.5 to about 1.5:1, or about 1:1.

The composition may contain mixtures of different types of conditioning actives. The compositions of the present disclosure may contain a certain conditioning active but be substantially free of others. For example, the composition may be free of quaternary ammonium ester compounds, silicones, or both. The composition may comprise quaternary ammonium ester compounds but be substantially free of silicone. The composition may comprise silicone but be substantially free of quaternary ammonium ester compounds.

The conditioning active may comprise glyceride copolymers. The glyceride copolymers may be derived from natural oils. Examples of natural oils include, but are not limited to, vegetable oils, algae oils, fish oils, animal fats, tall oils, derivatives of these oils, combinations of any of these oils, and the like. Representative non-limiting examples of vegetable oils include low erucic acid rapeseed oil (canola oil), high erucic acid rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil, preferably canola oil. Representative non-limiting examples of animal fats include lard, tallow, poultry fat, yellow grease, and fish oil. Tall oils are by-products of wood pulp manufacture. The glyceride copolymers may be metathesized unsaturated polyol esters.

C. Deposition Aid

The treatment compositions of the present disclosure may comprise a deposition aid. Deposition aids can facilitate deposition of the various benefit agents, including the multimer compounds of the present disclosure, conditioning actives, perfumes or perfume delivery systems (such as encapsulated perfumes), or combinations thereof, improving the performance benefits of the compositions and/or allowing for more efficient formulation of such benefit agents. The composition may comprise, by weight of the composition, from 0.0001% to 3%, preferably from 0.0005% to 2%, more preferably from 0.001% to 1%, or from about 0.01% to about 0.5%, or from about 0.05% to about 0.3%, of a deposition aid. The deposition aid may be a cationic or amphoteric polymer, preferably a cationic polymer.

Cationic polymers in general and their methods of manufacture are known in the literature. Suitable cationic polymers may include quaternary ammonium polymers known the "Polyquaternium" polymers, as designated by the International Nomenclature for Cosmetic Ingredients, such as Polyquaternium-6 (poly(diallyldimethylammonium chloride), Polyquaternium-7 (copolymer of acrylamide and diallyldimethylammonium chloride), Polyquaternium-10 (quaternized hydroxyethyl cellulose), Polyquaternium-22 (copolymer of acrylic acid and diallyldimethylammonium chloride), and the like.

The deposition aid may be selected from the group consisting of polyvinylformamide, partially hydroxylated polyvinylformamide, polyvinylamine, polyethylene imine, ethoxylated polyethylene imine, polyvinylalcohol, polyacrylates, and combinations thereof.

The cationic polymer may comprise a cationic acrylate and/or cationic methacrylate. Such polymers may be copolymers, for example further comprising a nonionic monomer, such as acrylamide. The cationic polymer may be linear or crosslinked. The deposition aid may comprise a combination of linear cationic polymers and crosslinked cationic polymers.

Deposition aids can be added concomitantly with delivery particles (at the same time with, e.g., encapsulated benefit agents, such as the encapsulated perfume) or directly/independently in the consumer product composition. The weight-average molecular weight of the polymer may be from 500 to 5000000 or from 1000 to 2000000 or from 2500 to 1500000 Dalton, as determined by size exclusion chromatography relative to polyethyleneoxide standards using Refractive Index (RI) detection. The weight-average molecular weight of the cationic polymer may be from 5000 to 37500 Dalton.

D. Perfume and/or Perfume Delivery Systems

The treatment compositions of the present disclosure may comprise perfume and/or perfume delivery systems. This may be the case even when the benefit agent residue of the multimer compound is derived from a perfume raw material.

The treatment compositions of the present disclosure may comprise other perfume raw materials, for example in neat or free form, including PRMs that do not contain an aldehyde or ketone moiety. For example, other PRMs may be provided as neat or free oils to the premix composition and/or the treatment compositions according to the present disclosure, even if they will not react with the multimer precursor compound. Such mixtures may be desirable, for example, to provide a more well-rounded olfactory experience.

The treatment compositions of the present disclosure may further comprise neat perfume, preferably neat perfume raw materials that does not comprise an aldehyde or ketone moiety. Preferably, the neat perfume comprises an alcohol-containing perfume raw material. Suitable alcohol-containing perfume raw materials are known to one of ordinary skill in the art, and may include geraniol, citronellol, cinnamic alcohol, eugenol, and the like. That being said, the neat perfume may further comprise free perfume raw materials that do comprise aldehyde and/or ketone moieties.

The treatment compositions of the present disclosure may, additionally or alternatively, comprise a perfume delivery system. Such perfume delivery systems may take the form of a polymer-assisted delivery system. Such perfume delivery systems may take the form of an encapsulate, for example a core-shell encapsulate, where the core comprises perfume raw materials and is surrounded by a polymeric shell. The polymeric shell may comprise polymeric material derived from polyacrylates, polyurea, polyurethanes, polysaccharides, polyvinyl alcohol, melamine, derivatives thereof, or combinations thereof. Additionally or alternatively, suitable perfume delivery systems may include known pro-perfume/pro-fragrance materials.

Other Materials

The treatment compositions, and/or even the premix compositions, of the present disclosure may comprise unreacted reactants and/or degradation products of the multimer compounds described herein. For example, the treatment compositions and/or premix compositions of the present disclosure may comprise: precursors or derivatives of the amino acid portions (such as parent amino acids), central linking groups that are reacted with zero or one amino acid portions, otherwise-free amino acids that include benefit agent residues, free benefit agents (such as aldehyde- or ketone-containing PRMs), or combinations thereof. It may be that multimer compounds and/or amino acid portions thereof react with other materials found in a formulation, for example where a benefit agent residue is replaced with the residue of a different material found in the formulation, particularly when such materials comprise aldehyde or ketone moieties; it is recognized that although unintentional, such reactions may occur in situ.

Premix

The present disclosure further relates to certain premix compositions and methods of making such compositions. Premixes can be conveniently prepared ahead of product formulation, and even prepared at one manufacturing site and shipped to another for product formulation.

The premix compositions may comprise a multimer precursor compound, where the multimer precursor compound is as described above, and a benefit agent, where the benefit agent is as described above. The preferences expressed above for the multimer compound, its components, and/or its precursors apply equally here. The premix composition may optionally comprise water. The premix composition may preferably further comprise a non-aqueous solvent, more preferably a hydroxyl-containing solvent, even more preferably ethanol.

For example, the premix composition may comprise: a modified amino acid multimer precursor compound, wherein the multimer precursor compound comprises a central linking group and from two to six amino acid portions that are each covalently linked to the central linking group by a (separate) heteroatom selected from the group consisting of O, S, and N, preferably O, wherein the central linking group comprises from 3 to 18 carbon atoms, wherein each amino acid portion comprises a carbon backbone comprising one or more carbon atoms, a carbonyl group that comprises a carbon atom, and a nitrogen atom, wherein the heteroatom is directly bonded to the carbon atom of the carbonyl group and to the central linking group; and a benefit agent, the benefit agent comprising an aldehyde moiety, a ketone moiety, or combinations thereof; and optionally water.

For example, the premix composition may comprise: a modified amino acid multimer precursor compound having a structure according to Formula I', $$L[E]_t \qquad \text{Formula I'},$$

wherein in L, E, and t are defined as above, with the proviso that the multimer precursor compound comprises at least two E groups that are moieties according to Formula II as defined above, with the further proviso that each A group of the moieties according to Formula II are selected from: (a) $H_2N$—, or (c) $HG'(J)_dN(H)$—, wherein G', J, and d are defined as above; and a benefit agent, the benefit agent comprising an aldehyde moiety, a ketone moiety, or combinations thereof; and optionally water. Other than for A, the preferences provided above for the remaining groups or indices equally apply to Formula I'.

For loading efficiency reasons, it is preferred to reasonably match the molar amount of the benefit agent, with the molar amount of the amino acid portions of the multimer precursor compound. As indicated above, a mole of multimer precursor compound will typically comprise from two to six moles of amino acid portion. When "X" represents the average number of amino acid portion equivalents per mole of precursor compound, then the premix composition may comprise the modified amino acid multimer precursor compound and the benefit agent in a molar ratio of from 1:0.5X to 1:2X, preferably from about 1:0.75X to about 1.5X, more preferably about 1:1X.

Even more specifically, for loading efficiency reasons, it is preferred to reasonably match the molar amount of the benefit agent with the molar equivalent of the reacting functional groups (e.g., the amine groups of the amino acid portions) of the carrier molecules as described above (here, the modified amino acid multimer precursor compound). For example, the premix composition may comprise the reacting functional groups (e.g., the amine groups) of the modified amino acid multimer precursor compound and benefit agent in a molar ratio of from about 3:1 to about 1:3, preferably from about 2:1 to about 1:2, preferably from about 1.5:1 to about 1:1.5, more preferably from about 1.2:1 to about 1:1.2, even more preferably about 1:1. When the modified amino acid multimer precursor compound comprises multiple attachment points, or multiple functional groups capable of forming such attachment points, for the benefit agent and optionally a second benefit agent, the premix composition may include such functional groups of the modified amino acid multimer precursor compound and the benefit agent (plus optionally an additional benefit agent that is also capable of attaching to the precursor compound, for example as the hydrophobe) present in a molar ratio of from about 3:1 to about 1:3, preferably from about 2:1 to about 1:2, preferably from about 1.5:1 to about 1:1.5, more preferably from about 1.2:1 to about 1:1.2, even more preferably from about 1:1.

The premix composition may be in the form of a neat fluid, and little to no water may be present. In such cases, it may be desirable to include a water scavenger such as magnesium sulfate in the premix, and/or to physically remove water, such as via a molecular sieve or in vacuo. The premix composition may comprise less than about 10%, preferably less than 5%, more preferably less than 1%, even more preferably less than 0.1% water, by weight of the premix composition. Low-water premix compositions may be particularly preferred when they are intended to be formulated into low-water product compositions, such as solids like pastilles, or compact formulations like unit dose compositions that are encapsulated in water-soluble films. When the premix is a low-water premix, the premix may comprise from about 1% to about 100%, preferably from about 5% to about 100%, more preferably from about 20% to about 100%, by weight of the premix composition, of the modified amino acid multimer precursor compound. When the premix is a low water premix, the premix may comprise from about 0.01% to about 80%, preferably from about 0.01% to about 20%, by weight of the premix composition, of the modified amino acid multimer precursor compound. When the premix is a low-water premix, the premix may comprise from about 0.01% to about 80%, preferably from about 0.01% to about 20%, by weight of the premix composition, of the benefit agent.

The premix composition may comprise a non-aqueous solvent, more preferably a hydroxyl-containing solvent, even more preferably ethanol. The premix composition may comprise, by weight of the premix composition, up to 50% solvent, preferably from about 5% to about 50%, more preferably from about 10% to about 25%, more preferably from about 10% to about 15%.

The premix composition may comprise water. The premix composition may be in the form of an emulsion, preferably an oil-in-water emulsion. When the premix is in the form of an emulsion and comprises water, water may be present at a level of from about 50% to about 95%, preferably from about 60% to about 90%, by weight of the premix composition. When the premix comprises water, the modified amino acid multimer precursor compound may be added at a level of from about 0.01% to about 7.5%, by weight of the premix composition. When the premix comprises water, the benefit agent may be added at a level of from about 0.01% to about 7.5%, by weight of the premix composition.

In the premix composition, the modified amino acid multimer precursor compound and the benefit agent may react to form a modified amino acid multimer compound, as described above. The precursor compound, the benefit agent, and the modified amino acid multimer compound may all be present in an equilibrium. Because the formation of certain modified amino acid multimer compounds, e.g., those comprising an imine, produces water through a condensation process, the equilibrium may be tilted towards the reactant side (e.g., precursor compound and benefit agent) of the reaction when the premix comprises water. Vice versa, relatively more of the modified amino acid multimer compound may be present when the premix is substantially free of intentionally added water, although it is recognized that some water forms as a result of the condensation reaction. Where the formation of the modified amino acid multimer compound involves a 1,4-addition, the equilibrium is not dependent on water, but rather is believed to depend on the balance between entropic and enthalpic contributions.

The sum of the weight percents of the modified amino acid multimer precursor, the benefit agent, and the modified amino acid multimer compound, if present, may be from about 10% to about 100%, preferably from about 25% to about 100%, preferably from about 50% to about 100%, more preferably from about 75% to about 100%, by weight of the premix composition.

The premix composition, or a portion thereof, may be obtained by combining from about 1 part to about 99 parts, preferably from about 5 to about 80 parts, by weight of the modified amino acid multimer precursor compound with about 1 part to about 99 parts, preferably from about 5 to about 80 parts, by weight of the benefit agent, wherein the resulting mixture is understood to comprise a total of 100 parts by weight.

The premix composition may include multiple precursors, multiple benefit agents, and/or multiple modified amino acid multimer compounds. The premix composition may further comprise additional agents that do not react to form modified amino acid multimer compounds according to the present disclosure. For example, the premix compositions may comprise additional PRMs, surfactants, solvents, antioxidants, or other processing or stability aids.

The premix composition may comprise a surfactant, preferably a nonionic surfactant. Surfactants may help with stability of the premix compositions, and/or with the emulsification process.

The present disclosure also relates to methods of making such premix compositions. The method may include the steps of combining a modified amino acid multimer precursor as described herein with a benefit agent as described herein, wherein the benefit agent comprises an aldehyde moiety, a ketone moiety, or a combination thereof. The materials may be combined in the proportions provided above. The method may include removing or otherwise binding free water, which may help to drive the reaction in the premix towards the product (e.g., the multimer compound). When the premix composition comprises water, the precursor compound and the water may preferably be combined before the benefit agent is added. Alternatively, the benefit agent and the water may be combined before the benefit agent is added.

Method of Making a Treatment Composition

The present disclosure relates to processes for making any of the compositions described herein. The process of making a treatment composition, which may be a consumer product, preferably a fabric care composition, may comprise the step of combining a modified amino acid multimer compound as described herein with an adjunct material as described herein.

The modified amino acid multimer compound may be combined with such adjunct materials by methods that include mixing and/or spraying.

The compositions of the present disclosure can be formulated into any suitable form and prepared by any process chosen by the formulator. The modified amino acid multimer compounds and adjunct materials may be combined in a batch process, in a circulation loop process, and/or by an in-line mixing process. Suitable equipment for use in the processes disclosed herein may include continuous stirred tank reactors, homogenizers, turbine agitators, recirculating pumps, paddle mixers, high shear mixers, static mixers, plough shear mixers, ribbon blenders, vertical axis granulators and drum mixers, both in batch and, where available, in continuous process configurations, spray dryers, and extruders.

For example, the method of making a treatment composition may include the step of combining a modified amino acid multimer compound according to the present disclosure with a base composition, preferably a liquid base composition, where the base composition comprises an adjunct ingredient. This process may occur, for example, in a batch process or in an in-line mixing process, preferably an in-line mixing process.

The method of making a treatment composition may include the step of combining a modified amino acid multimer precursor compound, a benefit agent, and an adjunct ingredient, as described herein. Preferably, the adjunct ingredient is part of a base composition, and the multimer precursor compound and the benefit agent are each added to the base composition as separate inputs. The separate inputs may be added sequentially (e.g., in series), or substantially simultaneously. Preferably, the base composition is a liquid. This process may occur, for example, in a batch process or in an in-line mixing process, preferably an in-line mixing process.

The method of making a treatment composition may include the step of adding a premix to a base composition. The premix composition may comprise a modified amino acid multimer precursor compound and a benefit agent, as described herein. The premix composition may be obtainable by combining a modified amino acid multimer precursor compound and a benefit agent, as described herein. The premix composition may include a modified amino acid multimer compound according to the present disclosure, for example due to the reaction of the precursor compound and the benefit agent. The premix composition may include a mixture of a modified amino acid multimer precursor compound, a benefit agent, and a modified amino acid multimer compound. The premix may optionally contain water. This process may occur, for example, in a batch process or in an in-line mixing process, preferably an in-line mixing process. A premix may be particularly preferred when making a treatment composition that is in, or will be in solid form, such as a PEG-based pastille. In such cases, removal or reduction of water from the premix may be useful, for example via a water scavenger such as magnesium sulfate, or via the use of a molecular sieve or distilled off in vacuo.

Method of Treating a Surface

The present disclosure further relates to methods of treating a surface (for example, a surface of an article) with a treatment composition according to the present disclosure. Such methods may provide cleaning, conditioning, hygienic, and/or freshening benefits.

Suitable surfaces may include fabrics (including clothing, towels, or linens), hard surfaces (such as tile, porcelain, linoleum or wood floors), dishware, hair, skin, or mixtures thereof.

The method may include a step of contacting an article or surface with a treatment composition of the present disclosure, optionally in the presence of water, optionally further including the step of rinsing and/or drying the article or surface. The treatment composition may be in neat form or diluted in a liquor, for example, a wash or rinse liquor. The treatment composition may be diluted in water prior, during, or after contacting the surface or article. The surface, or an article comprising such a surface, may be optionally washed and/or rinsed before and/or after the contacting step.

The method of treating and/or cleaning a surface may include the steps of:

a) optionally washing, rinsing and/or drying the surface;
b) contacting the surface with a treatment composition as described herein, optionally in the presence of water;
c) optionally washing and/or rinsing the surface; and
d) optionally drying the surface by drying passively and/or via an active method such as a laundry dryer.

For purposes of the present invention, washing includes but is not limited to, scrubbing, and mechanical agitation. The fabric may comprise most any fabric capable of being laundered or treated in normal consumer or industrial use conditions.

Liquors that may comprise the disclosed compositions may have a pH of from about 3 to about 11.5. When diluted, such compositions are typically employed at concentrations of from about 500 ppm to about 15,000 ppm in solution. When the wash solvent is water, the water temperature typically ranges from about 5° C. to about 90° C. and, when the surface is part of a fabric, the water to fabric weight ratio is typically from about 1:1 to about 30:1.

The present disclosure further discloses a process of treating a surface or article, preferably a fabric, with an aqueous treatment liquor that comprises a modified amino acid multimer compound according to the present disclosure, preferably where the benefit agent residue is a residue of a perfume raw material or an antimicrobial agent, preferably a residue of a perfume raw material. The process may include the step of contacting the surface or article, preferably a fabric, with the aqueous liquor. The multimer compound may be present in the aqueous liquor at a level of from about 0.001 ppm (e.g., 1 ppb) to about 1000 ppm by weight.

The present disclosure further discloses a process of treating a surface or article, preferably a fabric, with an aqueous treatment liquor that comprises the modified amino acid multimer precursor compound according to the present disclosure, and a benefit agent according to the present disclosure. The benefit agent may be a perfume raw material or an antimicrobial agent, preferably perfume raw material. The process may include the step of contacting the surface or article, preferably a fabric, with the aqueous liquor. The multimer precursor compound may be present in the aqueous liquor at a level of from about 0.001 ppm (e.g., 1 ppb) to about 1000 ppm by weight.

Use

The present disclosure relates to the use of the presently described modified amino acid multimer for providing a freshness benefit when the modified amino acid multimer comprises a residue of a perfume raw material, particularly when part of a treatment composition.

The present disclosure relates to the use of the presently described modified amino acid multimer compounds for providing an antimicrobial benefit when the modified amino acid multimer compound comprises a fragment of an antimicrobial agent, particularly when part of a treatment composition.

The present disclosure relates to the use of the presently described modified amino acid multimer compounds for providing an anti-malodor benefit, particularly when part of a treatment composition.

Combinations

Specifically contemplated combinations of the disclosure are herein described in the following lettered paragraphs. These combinations are intended to be illustrative in nature and are not intended to be limiting.

A. A treatment composition comprising: a treatment adjunct, and a modified amino acid multimer compound, wherein the multimer compound comprises a central linking group and from two to six amino acid portions each covalently linked to the central linking group by a heteroatom selected from the group consisting of O, S, and N, preferably O, wherein the central linking group comprises from 3 to 18 carbon atoms, wherein each amino acid portion comprises a carbon backbone comprising one or more carbon atoms, a carbonyl group that comprises a carbon atom, and a nitrogen atom, wherein the heteroatom is directly bonded to the carbon atom of the carbonyl group and to the central linking group, wherein at least one amino acid portion comprises an organic moiety covalently bonded to the nitrogen atom of the amino acid portion, wherein the organic moiety comprises a benefit agent residue, wherein when one or more bonds that connect the benefit agent residue to the amino acid portion are cleaved, a benefit agent is released, wherein the benefit agent comprises an aldehyde moiety, a ketone moiety, or a combination thereof.

B. A treatment composition comprising: a treatment adjunct, and a modified amino acid multimer compound, wherein the multimer compound comprises a central linking group and from two to six amino acid portions each covalently linked to the central linking group, wherein the central linking group comprises from 3 to 18 carbon atoms, wherein each amino acid portion comprises a carbonyl group at a C terminus, wherein the carbonyl group comprises a carbon atom, wherein the carbon atom of the carbonyl is bonded to a heteroatom of the central linking group, wherein the heteroatom is selected from the group consisting of O, S, or N, wherein each amino acid portion further comprises a nitrogen atom at an N terminus, wherein at least one amino acid portion comprises a benefit agent residue that is bonded to the nitrogen atom at the N terminus of the at least one amino acid portion, wherein a benefit agent is released when one or more bonds that connect the benefit agent residue to the amino acid portion are cleaved, wherein the benefit agent comprises an aldehyde moiety, a ketone moiety, or a combination thereof.

C. The treatment composition according to any of paragraphs A or B, wherein the carbon backbone of each amino acid portion independently comprises from 1 to 9 carbon atoms, preferably from 1 to 6 carbon atoms, more preferably from 1 to 3 carbon atoms, more preferably 1 to 2 carbon atoms, even more preferably 1 carbon atom.

D. The treatment composition according to any of paragraphs A-C, wherein at least one, preferably at least two, more preferably all, of the amino acid portions are derived from proteogenic amino acids, preferably proteogenic amino acids independently selected from cysteine, glycine, aspartic acid, glutamic acid, lysine, or combinations thereof, more preferably cysteine.

E. The treatment composition according to any of paragraphs A-D, wherein the amino acid portions are derived from amino acids having the same identity, preferably derived from proteogenic amino acids having the same identity.

F. The treatment composition according to any of paragraphs A-E, wherein at least two, preferably all, of the amino acid portions comprise a benefit agent residue.

G. A treatment composition comprising: a treatment adjunct, and a modified amino acid multimer compound, wherein the modified amino acid multimer compound is characterized by a structure according to Formula I:

$L[E]_t$ Formula I, wherein t is independently an integer from 2 to 6, preferably 2 to 5, more preferably 2 to 4, more preferably 2 to 3, more preferably 2; wherein L is a central linking group that is multivalent and that comprises 3 to 18 carbon atoms; wherein each E group is independently selected from -GH, -GX, or a moiety according to Formula II:

Formula II

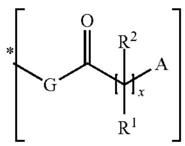

with the proviso that the multimer compound comprises at least two E groups that are moieties according to Formula II, wherein * indicates the point of attachment of the E group with L, wherein the value of x is from 1 to 9, preferably from 1 to 6, more preferably from 1 to 3, even more preferably from 1 to 2, even more preferably 1, wherein each G is independently selected from the group consisting of —O—, —$N(R^3)$—, or —S—, preferably wherein each G group is the same, wherein each $R^3$, if present, is independently selected from H or a monovalent moiety with a molecular weight between 14 and 881 Da, preferably between 41 and 255 Da, wherein X, if present, is a suitable charge-balancing counterion, wherein each $R^1$ is independently selected from H or a monovalent moiety with a molecular weight between 15 and 507 Da, preferably $R^1$ is selected from a side group of a proteogenic amino acid or a monovalent moiety with a molecular weight between 15 and 142 Da; wherein each $R^2$ is independently selected from H and a monovalent moiety with a molecular weight of between 15 and 1000 Da, preferably from 15 to 507 Da, more preferably from 15 to 142 Da, preferably wherein $R^2$ is H, wherein each A group is a monovalent nitrogen-comprising moiety, wherein at least one A group comprises an independently selected benefit agent residue that is linked to the rest of the A group by one or more bonds, wherein a benefit agent is released when the one or more bonds are cleaved, wherein the benefit agent comprises an aldehyde moiety, a ketone moiety, or a combination thereof.

H. The treatment composition according to paragraph G, wherein each A group is independently selected from the group consisting of: (a) $H_2N$—; (b) ZN—, wherein  represents a linking bond between the nitrogen atom and a carbon atom of the Z group, wherein the linking bond is one of: (i) a double bond, thereby forming an imine bond, or (ii) a single bond formed from a 1,4-addition when the benefit agent from which the benefit agent residue is derived comprises an alpha-beta unsaturated carbonyl-containing moiety that is an aldehyde moiety or a ketone moiety, wherein the nitrogen atom of the Z**N— group is further bonded to a hydrogen (—H); (c) $HG'(J)_dN(H)$—; and (d)

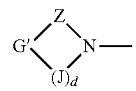

wherein the index d is selected from 1 to 3, preferably d is from 2 to 3, more preferably d is 2; wherein each G' is independently selected from —O—, —S—, or —$N(R^7)$—, preferably wherein G' is —O—, wherein each $R^7$, if present, is independently selected from —H or a monovalent moiety with a molecular weight of from about 15 to about 255 Da, preferably wherein $R^7$ is a monovalent moiety with a molecular weight of from about 15 to about 142 Da, more preferably a monovalent moiety with a molecular weight from about 15 to about 30 Da, wherein the Z group comprises from 4 to 34 carbon atoms, and wherein the N and the G' are bonded to the same carbon atom of the Z group, wherein each J is independently selected from the group consisting of $C(R^9)_2$, —O—, and —$N(R^9)$, preferably each J is $C(R^9)_2$, wherein each $R^9$ is independently selected from H or a monovalent moiety with a molecular weight between 14 and 990 Da, more preferably $R^9$ is selected from H or a monovalent moiety with a molecular weight between 14 and 186 Da, even more preferably $R^9$ is H, with the proviso that a first $R^9$ and a second $R^9$ can optionally be taken together, where feasible, as a divalent substituent, preferably where the divalent substituent is selected from the group consisting of a fused ring, a spirocyclic ring, and an unsaturated substituent selected from $=N(R^7)$, =O, and =S, wherein $R^7$, if present, is as defined above, wherein at least one A group is independently selected from (b) or (d), more preferably at least one A group is selected from (b) ZN—, even more preferably all A groups are selected from (b) ZN—; wherein each Z group is the independently selected benefit agent residue.

I. The treatment composition according to paragraph H, wherein at least one A group is selected from (b) ZN—, and wherein the Z group of the ZN-moiety is independently selected from the group consisting of

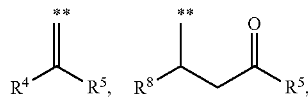

and mixtures thereof, wherein the —$C(R^4)(R^5)$ and —$CH(R^8)CH_2C(O)R^5$ moieties each represent a residue of a benefit agent, wherein the residue of the benefit agent has a molecular formula that differs from the molecular formula of the benefit agent only by having one less O atom or one more H atom, wherein the benefit agent comprises an aldehyde moiety, a ketone moiety, or a combination thereof, preferably wherein $R^4$ is independently selected from a monovalent organic moiety, and wherein $R^5$ and $R^8$ are independently selected from the group consisting of hydrogen and a monovalent organic moiety, more preferably wherein the benefit agent is a perfume raw material comprising from 4 to 34 carbon atoms, with the proviso that $R^4$ and $R^5$, or $R^8$ and $R^5$, may combine to form a cyclic divalent organic moiety.

J. The treatment composition according to any of paragraphs G-I, wherein the Z group is a benefit agent residue having the following structure:

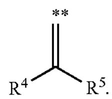

K. The treatment composition according to any of paragraphs G-J, wherein at least one of the following is true: more than one A group comprises a benefit agent residue; for a given compound, the identity of the A groups are identical; for a given compound, the identity of the A groups are different; wherein for a given compound, the identity of the Z groups are identical; and/or wherein for a given compound, the identity of the Z groups are different.

L. The treatment composition according to any of paragraphs G-K, wherein at least one $R^2$ comprises a residue of an additional benefit agent, preferably wherein the $R^2$ that comprises the residue is a monovalent moiety with a molecular weight of from 54 and 1000 Da.

M. The treatment composition according to any of paragraphs A-L, wherein the central linking group comprises from 3 to 16 carbon atoms, preferably from 5 to 12 carbon atoms, more preferably 8 to 12 carbon atoms.

N. The treatment composition according to any of paragraphs A-M, wherein the central linking group is a divalent, trivalent, or tetravalent organic moiety, preferably divalent.

O. The treatment composition according to any of paragraphs A-N, wherein the central linking group is derived from a polyhydric alcohol, preferably selected from a diol, a triol, or pentaerythritol, even more preferably selected from: 1,6-hexanediol; 1,8-octanediol; 1,10-decanediol; 1,12-dodecanediol; glycerol; or pentaerythritol.

P. The treatment composition according to any of paragraphs A-O, wherein the benefit agent residue is a residue of a benefit agent selected from a perfume raw material, an antimicrobial agent, a pesticide, an insect repellant, an anti-fungal agent, a herbicidal agent, a hueing dye, an antioxidant, a non-perfume organoleptic, or a combination thereof, preferably a perfume raw material, an antimicrobial agent, or combinations thereof.

Q. The treatment composition according to any of paragraphs A-P, wherein the benefit agent is a perfume raw material, preferably a perfume raw material selected from the group consisting of: methyl nonyl acetaldehyde: benzaldehyde; floralozone; isocyclocitral; triplal (ligustral); precyclemone B; lilial; decyl aldehyde; undecylenic aldehyde; cyclamen homoaldehyde; cyclamen aldehyde; dupical; oncidal; adoxal; melonal; calypsone; anisic aldehyde; heliotropin; cuminic aldehyde; scentenal; 3,6-dimethylcyclohex-3-ene-1-carbaldehyde; satinaldehyde; canthoxal; vanillin; ethyl vanillin; cinnamic aldehyde; cis-4-decenal; trans-4-decenal; cis-7-decenal; undecylenic aldehyde; trans-2-hexenal; trans-2-octenal; 2-undecenal; 2,4-dodecadeienal; cis-4-heptenal; Florydral; butyl cinnamaldehyde; limonelal; amyl cinnamaldehyde; hexyl cinnamaldehyde; citronellal; citral; cis-3-hexen-1-al; nerolione; 4-(4-methoxyphenyl) butan-2-one; 1-naphthalen-2-ylethanone; nectaryl; trimofix O; fleuramone; delta-damascone; beta-damascone; alpha-damascone; methyl ionone; 2-hexylcyclopent-2-en-1-one; galbascone; and mixtures thereof.

R. The treatment composition according to any of paragraphs A-Q, wherein the modified amino acid multimer compound comprises a polymeric component of three or more repeating units.

T. The treatment composition according to any of paragraphs A-S, wherein the adjunct ingredient comprises a conditioning active, preferably wherein the conditioning active comprises quaternary ammonium ester compounds, more preferably wherein the quaternary ammonium ester compounds are present at a level of from about 2 wt % to about 35 wt %, preferably from about 4 wt % to about 25 wt %, more preferably from about 5 wt % to about 20 wt %, preferably from about 6 wt % to about 15 wt %, more preferably from about 7 wt % to about 12 wt %, by weight of the treatment composition.

S. The treatment composition according to any of paragraphs A-R, wherein the adjunct ingredient comprises one or more of the following: surfactants, conditioning actives, deposition aids, rheology modifiers or structurants, antioxidants, bleach systems, stabilizers, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, silicones, hueing agents, aesthetic dyes, neat perfume, perfume delivery systems, structure elasticizing agents, carriers, hydrotropes, processing aids, anti-agglomeration agents, coatings, formaldehyde scavengers, and/or pigments.

U. The treatment composition according to any of paragraphs A-T, wherein the treatment composition further comprises neat perfume, preferably neat perfume that comprises an alcohol-containing perfume raw material, an ester-containing perfume raw material, or combination thereof.

V. The treatment composition according to any of paragraphs A-U, wherein the treatment composition is a consumer product, preferably a consumer product selected from a fabric care composition, a hard surface cleaner composition, a dish care composition, a hair care composition, a body cleansing composition, or a mixture thereof, even more preferably a fabric care composition.

W. The treatment composition according to any of paragraphs A-V, wherein the treatment composition is in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam or mousse, a non-woven sheet, or a mixture thereof.

X. The treatment composition according to any of paragraphs A-W, wherein the multimer compound is present in the treatment composition at a level of from about 0.001% to about 30%, by weight of the treatment composition.

Y. A modified amino acid multimer compound according to any of paragraphs A-X.

Z. A modified amino acid multimer precursor compound having a structure according to Formula I', $$L[E]_t \qquad \text{Formula I'},$$

wherein L, E, and t are defined as above, with the proviso that the multimer precursor compound comprises at least two E groups that are moieties according to Formula II as defined above, with the further proviso that each A group of the moieties according to Formula II are selected from: (a) $H_2N$—, or (c) $HG'(J)_dN(H)$—, wherein G', J, and d are defined as above.

AA. A premix composition comprising a modified amino acid multimer precursor compound according to paragraph Z, a benefit agent, and optionally water, wherein the benefit agent comprises an aldehyde moiety, a ketone moiety, or a combination thereof; wherein the premix composition optionally further comprises a non-aqueous solvent, more preferably a hydroxyl-containing solvent, even more preferably ethanol.

BB. A method of making a treatment composition according to any of paragraphs A-X, wherein the method comprises at least one of the following: (a) combining a modified amino acid multimer compound with an adjunct ingredient, preferably wherein the adjunct ingredient is part of a base composition; (b) combining a premix composition according to paragraph AA with an adjunct ingredient, preferably wherein the adjunct ingredient is part of a base composition; (c) combining a modified amino acid multimer precursor compound, a benefit agent, and an adjunct ingredient, preferably wherein the adjunct ingredient is part of a base composition and the modified amino acid multimer compound and the benefit agent are each added to the base composition as separate inputs.

CC. A method of treating an article or a surface, wherein the method comprises treating the article or surface with a treatment composition according to any of paragraphs A-X, optionally in the presence of water, optionally further including the step of rinsing and/or drying the article or surface.

Test Methods

It is understood that the test methods disclosed in the Test Methods section of the present application should be used to determine the respective values of the parameters of Applicant's claimed subject matter as claimed and described herein.

HLB Value of Nonionic Surfactants

Nonionic surfactants can be classified by the balance between the hydrophilic and lipophilic moieties in the surfactant molecule. The hydrophile-lipophile balance (HLB) scale devised by Griffin in 1949 is a scale from 0-20 (20 being Hydrophilic) used to characterize the nature of surfactants. The HLB of a surfactant may be calculated as follows:

$$HLB=20*Mh/M$$

where Mh is the molecular of the hydrophilic portion of the molecule, and M is the molecular mass of the whole molecule, giving a result on a scale of 0 to 20. An HLB value of 0 corresponds to a completely lipophilic/hydrophobic molecule, and a value of 20 corresponds to a completely hydrophilic/lipophobic molecule. See Griffin, W. C. Calculation of HLB values of Nonionic Surfactants, J. Soc. Cosmet. Chem. 1954, 5, 249-256. The HLB values for commonly-used surfactants are readily available in the literature (e.g., HLB Index in McCutcheon's Emulsifiers and Detergents, MC Publishing Co., 2004). The HLB value for a mixture of surfactants can be calculated as a weighted average of the HLB values of the surfactants.

Test Method for Determining log P

The value of the log of the Octanol/Water Partition Coefficient (log P) is computed for a material (such as the alcohol version of a hydrophobe/Q group, or of a PRM) as described here.

The log P of an individual material is calculated using the Consensus log P Computational Model, version 14.5 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Preparation of a Test Fabric Enhancer/Softener Composition

A 7.5 wt % N,N-di(tallowoyloxyethyl)-N,N-dimethylammonium chloride in water mixture is provided. A premix fluid as described above, a premix emulsion as described above, or two discrete neat fluids (one being the multimer precursor, such as a modified amino acid; the other being the benefit agent, such as one or more perfume raw materials) are added in an amount such that the concentration of the benefit agent or benefit material fragment in the fabric softener is about 0.3 wt % of the final fabric softener composition. The mixture is stirred for 5 min with an IKA RW 20 D S1 Mixer, Model RW20DS1, and IKA RI 342 impeller blade at 350 rpm. A structurant and a deposition aid is added, and the mixture is stirred for 10 min. Water is added if needed to standardize the concentration of N,N di(tallowoyloxyethyl)-N,N dimethylammonium chloride amongst test legs to 7.3 wt %, and the mixture stirred for 5 min. The pH is adjusted to 2-3 with HCl, if necessary.

Preparation of a Test Fabric Detergent Composition

To 97.58 parts by weight of TIDE Original Scent liquid detergent, formulated without TIDE OS perfumes, is added 2.42 parts by weight of the multimer compound premix fluid. The amount is selected such that the concentration of the selected benefit agent or benefit material fragment in the final detergent is about 1 wt % after the fabric treatment composition. The mixture is stirred for 10 min with an IKA RW 20 D S1 Mixer, Model RW20DS1, and IKA RI 342 impeller blade at 350 rpm.

Fabric Preparation Method

To prepare fabrics for Headspace analysis testing, fabric samples (100% Cotton Terry Cloth, Item Number ITL 1022-15PGP, CalderonTextiles, Inc. 6131 W. 80tA St., Indianapolis, Ind. 46278, Desized and conditioned with 3 wash cycles of Detergent and Fabric Softener) are treated with the detergents or fabric conditioners in a manner consistent with North American consumers via clothes mini-washing machines, full scale machines, and clothes dryers. Fabric are equilibrated at 21.1° C. and 50% relative humidity for 12 to 24 hours, unless noted otherwise, prior to Headspace GCMS analysis (see methods below). Ballast loads are comprised of cotton and polycotton knit swatches approximately 20×20 inches (50×50 cm) in size.

Wash Treatment Conditions

In the fabric enhancer/softener compositions performance tests below, the fabrics are treated with the following wash treatment conditions: Wash: 12 min agitation, 30.6° C. Rinse: 2 min agitation, 15.5° C. Water Hardness: 137 ppm. Water: 7.6 pH. Fabric Load Weight: 290 g. Tumble Dry Setting: 50 min High, Cotton. Detergent Dose: 9.65 g. Fabric Softener Dose: 5.71 g.

The detergent used is TIDE Original Scent liquid without perfume (produced by The Procter & Gamble Company).

Headspace Analysis Above Fabrics

To determine the level of benefit agent material in the headspace above a fabric, the following procedure is used.

The following equipment is used: Gas Chromatograph 7890B equipped with a Mass Selective Detector (5977B) (MSD) and Chemstation quantitation package; Gerstel Multi-Purpose sampler equipped with a solid phase microextraction (SPME) probe or similar system; Divinylbenzene/Carboxen/Polydimethylsiloxane SPME fiber from Supleco part #57298-U (or similar fiber); 30 m×0.25 mm nominal diameter, 0.25 m film thickness, J&W 122-5532UI DB-5; 20 mL headspace vials.

To prepare the fabric for analysis, cut three 2.54 cm×5.08 cm cotton swatches from the cotton terry that is prepared and treated according to the above methods. Place each piece in a 20 mL headspace vial and cap.

The Gerstel auto sampler parameters are as follows: SPME—from Incubator; Incubation Temperature—65° C.; Incubation Time—10.00 min SAMPLE PARAMETERS; Vial Penetration 22.00 mm; Extraction Time—5.00 min; Ini. Penetration—54.00 mm; Desorption Time—300 s. The GC oven parameters are as follows for the Front SS Inlet He: Mode—Splitless; Heater—270° C.; GC Run Time—14.28 min. For the Oven: Initial temp.—40° C.; Hold Time—0.5 min; Heating Program—Rate of 17° C./min, Temp of 270° C., Hold Time of 0.25 min. The MSD parameters are as follows: Run in scan mode with a minimum range of 35 to 350 m/z.

Calibration curves are generated from the standards benefit agent material. Chemstation software (or similar quantitation software) calculates the mass amount in the headspace using the calibration curve for each perfume component.

EXAMPLES

The examples provided below are intended to be illustrative in nature and are not intended to be limiting.

Synthesis Examples

The following Synthetic Examples 1-5 exemplify the synthesis of illustrative pro-benefit-agent compounds (e.g., Synthetic Example 1) and their amine-containing pro-fragrance precursor (e.g., Synthetic Example 1'), according to the present disclosure.

For consistency and illustrative/comparative purposes, each example reacts a different neat pro-fragrance precursor molecule with the same perfume raw material, cyclamen aldehyde (containing an aldehyde moiety), which has the following structure. As an additional example (one formed through 1,4 addition), Synthetic Example 1B forms a pro-benefit-agent compound with 8-damascone, which contains a ketone moiety. The structures of the PRMs are provided below:

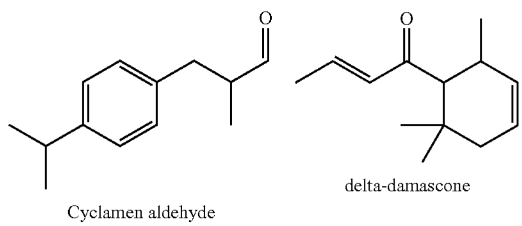

Cyclamen aldehyde delta-damascone

However, it is understood that other aldehyde- or ketone-containing benefit agents according to the present disclosure may also lead to the formation of suitable pro-benefit-agent compounds; some of these are exemplified and tested in the Performance Examples below.

It is also understood that the Synthetic Examples may be formulated into a treatment composition as a liquid premix emulsion or as a neat fluid or as a liquid premix fluid as described above; however, for the case of the reported performance and stability examples below, all Synthetic Examples are assumed to be formulated directly as liquid premix fluids into the treatment composition unless indicated otherwise.

For each Synthetic Example, the resulting pro-benefit-agent compound (e.g., a modified amino acid ester molecule) is illustrated with cyclamen aldehyde (or in the case of Synthetic Example 1B, 8-damascone) and provided below in Table D.

Methods of Preparing Modified Amino Acid Multimer Compounds

In the following synthesis examples, the materials are generally obtained/available from Sigma-Aldrich (St. Louis, MO, USA), except as indicated below. The amino acids are generally provided at >98% or even >99% purity. The alcohols are generally provided at >97%, >98%, or even >99% purity. Cyclamen aldehyde (ex Sigma-Aldrich) is provided at >95% purity. 8-Damascone is available from Firmenich of Geneva, Switzerland.

General Method A: General Preparation of Multimer Precursor Compound

To prepare a multimer precursor compound from an amino acid and an alkyl alcohol (e.g., glycerol), a round bottom flask is charged with about 1 equiv. of a free base amino acid starting material. To the flask is added the indicated equivalence of an alcohol and about 1.2 equiv. of p-Toluene-sulfonic acid monohydrate (PTSA) or Methanesulfonic acid (MsOH). The flask is then diluted with toluene and refluxed for 12 h using a dean-stark apparatus. Solvent is removed in vacuo and the resulting crude material dissolved in chloroform. The solution is neutralized with $Et_3N$, then washed 3× with NaOH, and dried over $MgSO_4$. Solvent is removed and the washed material is diluted with cyclohexane, stored at 0° C. for 12 h. The eluent is collected yielding the desired modified amino acid (ester) multimer precursor compound.

General Method B: General Preparation of Modified Amino Acid Multimer Compound

A round bottom flask is charged with 1 equiv. of a modified amino acid multimer precursor. To the flask is added 1 equiv. of either cyclamen aldehyde or 8-damascone. To the fluid is added 20 wt % 4 Å molecular sieves and the mixture stirred for 12 h. The resulting mixture is filtered using a Pyrex 36060-30M Brand 36060 fritted funnel and used directly.

Synthetic Example 1A

Synthetic Example 1' was prepared as described in General Method A, but using 10 g of DL-Valine, 6.0 g of 1,10-decanediol, and 8.2 g PTSA·$H_2O$. The isolated fluid of Synthetic Example 1' was then mixed with cyclamen aldehyde as described in General Method B yielding Synthetic Example 1A. The independent fluid 1A appears stable for several months by $^1H$ NMR.

Synthetic Example 1B

Synthetic Example 1' was prepared as described in Synthetic Example 1A. The isolated fluid of Synthetic Example 1' was then mixed with 8-damascone as described in General Method B yielding Synthetic Example 1B. The independent fluid 1B appears stable for several months by $^1H$ NMR.

Synthetic Example 2

Synthetic Example 2' was prepared as described in General Method A, but using 10 g of L-Valine, 5.3 g of 1,12-dodecanediol, and 8.2 g PTSA·$H_2O$. The isolated fluid of Synthetic Example 2' was then mixed with cyclamen aldehyde as described in General Method B yielding Synthetic Example 2. The independent fluid 2 appears stable for several months by $^1H$ NMR.

Synthetic Example 3

Synthetic Example 3' was prepared as described in General Method A, but using 10 g of L-Valine, 1.7 g of pentaerythritol, and 20 g PTSA·$H_2O$. The isolated fluid of Synthetic Example 3' was then mixed with cyclamen aldehyde as described in General Method B yielding Synthetic Example 3. The independent fluid 3 appears stable for several months by $^1H$ NMR.

Synthetic Example 4

Synthetic Example 4' was prepared as described in General Method A, but using 26 g of L-Valine, 5.0 g of glycerol, and 44 g PTSA·$H_2O$. The isolated fluid of Synthetic Example 4' was then mixed with cyclamen aldehyde as described in General Method B yielding Synthetic Example 4. The independent fluid 4 appears stable for several months by $^1H$ NMR.

Synthetic Example 5

Synthetic Example 5' was prepared as described in General Method A, but using 20 g of L-phenylalanine, 9.8 g of 1,12-dodecanol, and 25 g PTSA·$H_2O$. The isolated fluid of Synthetic Example 5' was then mixed with 8-damascone as described in General Method B yielding Synthetic Example 5. The independent fluid 5 appears stable for several months by $^1H$ NMR.

Structures of the Synthetic Examples

Table D below illustrates the structures of the Synthetic Examples 1-5, as well as their precursor compounds (denoted with a “'”).

TABLE D

Structural representation of the Synthesis Examples

| No. | Precursor Compound (e.g., before the addition of a benefit agent) | No. | Pro-Benefit-Agent Compound (e.g., a compound according to Formula 1 or Formula 2) |
|---|---|---|---|
| 1' | 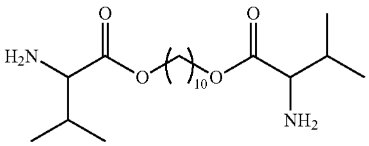 | 1A | 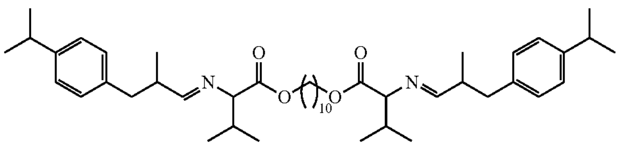 |
| | | 1B | 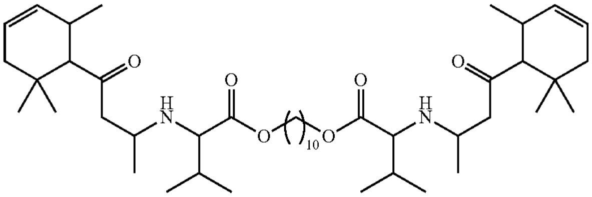 |
| 2' | 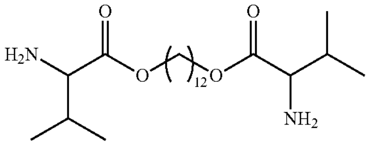 | 2 | 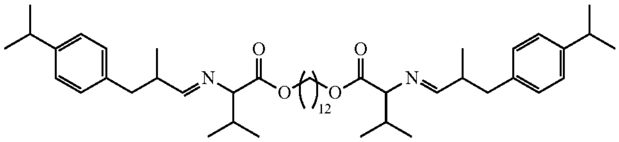 |
| 3' | 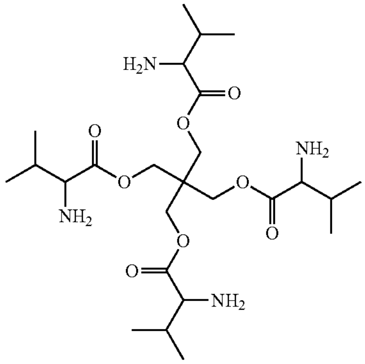 [SMILES: CC(C)C(N)C(=O)OCC(COC(=O)C(N)C(C)C)(COC(=O)C(N)C(C)C)COC(=O)C(N)C(C)C] | 3 | 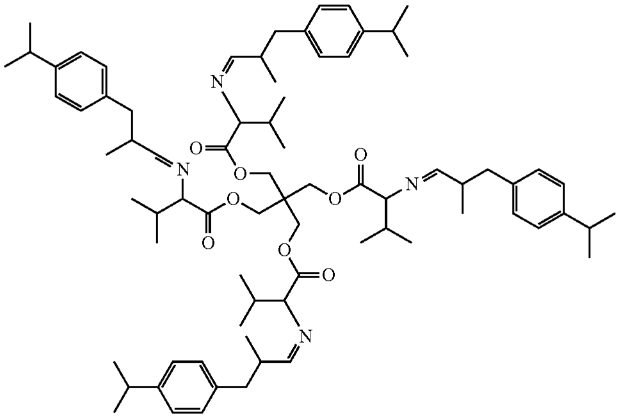 [SMILES: CC(C=NC(C(=O)OCC(COC(=O)C(N=CC(C)Cc1ccc(C(C)C)cc1)C(C)C)(COC(=O)C(/N=C\C(C)Cc1ccc(C(C)C)cc1)C(C)C)COC(=O)C(/N=C\C(C)Cc1ccc(C(C)C)cc1)C(C)C)C(C)C)Cc1ccc(C(C)C)cc1] |

TABLE D-continued

| Structural representation of the Synthesis Examples | | | |
|---|---|---|---|
| No. | Precursor Compound (e.g., before the addition of a benefit agent) | No. | Pro-Benefit-Agent Compound (e.g., a compound according to Formula 1 or Formula 2) |
| 4' | 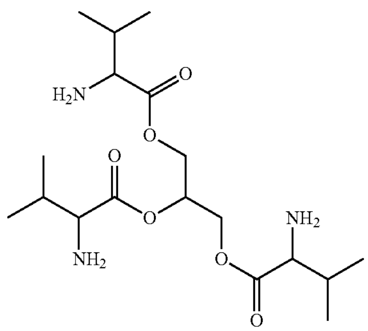 [SMILES: CC(C)C(N)C(=O)OCC(COC(=O)C(N)C(C)C)OC(=O)C(N)C(C)C] | 4 | 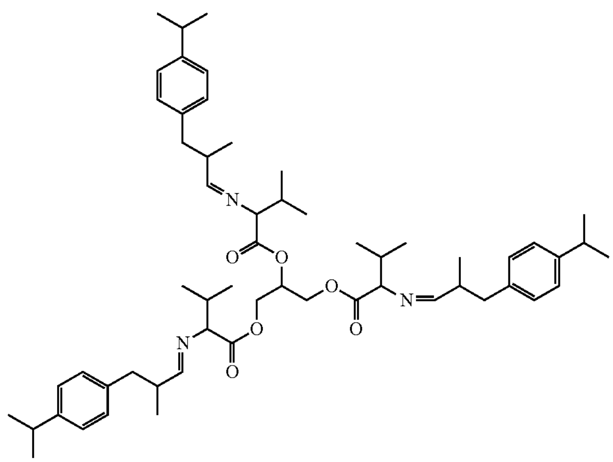 [SMILES: CC(C=NC(C(=O)OC(COC(=O)C(/N=C\C(C)Cc1ccc(C(C)C)cc1)C(C)C)COC(=O)C(/N=C/C(C)Cc1ccc(C(C)C)cc1)C(C)C)C(C)C)Cc1ccc(C(C)C)cc1] |
| 5' | 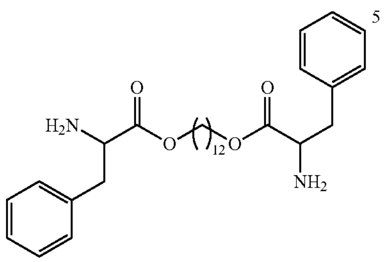 | 5 | 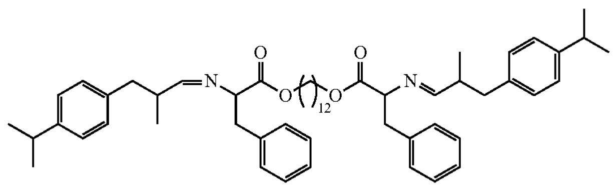 |

In the following Performance Examples, pro-benefit-agent precursor compounds (e.g., amino acid ester molecules) and the indicated perfume raw materials are mixed substantially following a procedure aligned with the method found in the Test Methods section above ("Preparation of a Premix Fluid"). Despite the different methods of preparation (e.g., made with different pro-benefit agents) between the Synthesis Examples and the Performance Examples, the inputs and outputs, in terms of the pro-benefit-agent compounds, are substantially the same.

Performance Examples

In Performance Examples 1-3 below, treatment compositions comprising neat perfume oil, or pro-benefit-agent compounds according to the present disclosure (e.g., based on modified amino acid multimers), are compared via treatment cycles in an automatic washing machine according to the Fabric Treatment methods provided above. After treatment, the fabrics are tested for Headspace Analysis according to the test methods provided above. The data below shows the benefits afforded by hydrophobically modified amino acid esters, and their interaction with benefit agents through an imine or 1,4-adduct, in delivering benefit agents.

Performance Example 1. Application in Liquid Fabric Enhancers with a Series of Modified Amino Acid Esters To further evaluate these materials, a range of benefit agent materials were examined. In the examples below, equal molar concentrations of aldehydic benefit agents, described in the respective test legs, are provided to a precursor amino acid as describe above, then formulated into a Test Fabric Enhancer/Softener Composition, prepared as provided in the test methods above. Test fabrics are prepared, wash treated, and tested for headspace analysis above the fabrics according to the test methods above.

It is understood that for the rows reading "Synthetic Example 1," etc., both in Table 1 and in subsequent tables, the sample was prepared substantially in accordance with the method and precursor provided in the listed Synthetic Example, but with the benefit agent materials listed in the performance table (in equal molar concentrations to the precursor modified amino acid ester) rather than with just cyclamen aldehyde or 8-damascone, and formulated as a premix fluid as detailed above.

Results of the Headspace Analysis Above Fabrics testing are provided below in Table 1.

TABLE 1

| Average headspace concentration of aldehyde benefit agents[a] above fabrics | | | | | |
|---|---|---|---|---|---|
| Compound | Amount of Methyl Nonyl Acetaldehyde released (nmol/L) | Amount of Floralozone released (nmol/L) | Amount of P.T. Bucinal released (nmol/L) | Amount of Precyclemone B released (nmol/L) | Total Headspace Amount released (nmol/L) |
| Neat Raw Materials | 3.51 | 0.18 | 2.35 | 0.41 | 6.45 |
| Synthetic Example 1 | 18.09 | 5.86 | 8.29 | 6.75 | 38.99 |
| Synthetic Example 2 | 25.57 | 10.06 | 11.23 | 11.59 | 58.45 |

[a]The formulation of the accord is at 0.3 wt % and is composed as follows: 10 wt % Methyl nonyl acetaldehyde, 40 wt % P.T. Bucinal, 20 wt % Precyclemone B, and 30 wt % Floralozone.

As shown in Table 1, the hydrophobically modified amino acid esters 1 and 2 delivered an improvement in total headspace over neat raw materials.

Furthermore, increasing carbon chain length provides an improvement in overall delivery of benefit agents as exemplified by Synthetic Examples 2. Synthetic Example 2 showed the highest improvement in head space. Overall, the Synthetic Examples show a similar trend in delivery individual benefit agents.

Performance Example 2. Comparative Example of Dimers, Trimers, and Tetramers a Liquid Fabric Enhancer Formulation In the examples below, equal molar concentrations of aldehydic benefit agents, described in the respective test legs, are provided to a precursor amino acid as describe above, then formulated into a Test Fabric Enhancer/Softener Composition, prepared as provided in the test methods above. Test fabrics are prepared, wash treated, and tested for headspace analysis above the fabrics according to the test methods above. Results of the Headspace Analysis Above Fabrics are provided in Table 2.

TABLE 2

| Average headspace concentration of aldehyde benefit agents[a] above fabrics | | | | | |
|---|---|---|---|---|---|
| Compound | Amount of Methyl Nonyl Acetaldehyde released (nmol/L) | Amount of Floralozone released (nmol/L) | Amount of P.T. Bucinal released (nmol/L) | Amount of Precyclemone B released (nmol/L) | Total Headspace Amount released (nmol/L) |
| Neat Raw Materials | 1.32 | 0.06 | 1.69 | 0.43 | 3.50 |
| L-Phenylalanine | 2.89 | 0.13 | 3.53 | 1.23 | 7.77 |
| Synthetic Example 3 | 7.28 | 0.89 | 7.35 | 5.44 | 20.96 |
| Synthetic Example 4 | 6.45 | 0.95 | 10.24 | 6.86 | 24.49 |
| Synthetic Example 5 | 8.86 | 3.12 | 9.02 | 12.67 | 33.67 |

[a]The formulation of the accord is at 0.3 wt % and is composed as follows: 10 wt % Methyl nonyl acetaldehyde, 40 wt % P.T. Bucinal, 20 wt % Precyclemone B, and 30 wt % Floralozone.

As shown in Table 2, modified amino acid materials provide a significant benefit over neat oils or the free base amino acids. Furthermore, for this particular performance test, the phenylalanine dimer outperformed either the trimer or tetramers.

Trends in individual benefit agents are different across the different modified amino acids. Thus, it would appear plausible to configure a singular or mixture of systems containing combinations of benefit agent, amino acid, and a (preferably hydrophobic) central linking group to drive desirable benefits.

Performance Example 3. Comparative Example of Modified Amino Acids in a Detergent Composition In the examples below, equal molar concentrations of aldehydic benefit agents, described in the respective test legs, are provided to a precursor amino acid as describe above, then formulated into a Test Fabric Detergent Composition, prepared as provided in the test methods above. Test fabrics are prepared, wash treated, and tested for headspace analysis above the fabrics according to the test methods above. Results of the Headspace Analysis Above Fabrics are provided in Table 3.

TABLE 3

Average headspace concentration of aldehyde benefit agents [a] above fabrics

| Compound | Amount of Methyl Nonyl Acetaldehyde released (nmol/L) | Amount of Floralozone released (nmol/L) | Amount of P.T. Bucinal released (nmol/L) | Amount of Precyclemone B released (nmol/L) | Total Headspace Amount released (nmol/L) |
|---|---|---|---|---|---|
| Neat Raw Materials | 1.48 | 0.05 | 1.64 | 1.26 | 4.44 |
| Synthetic Example 3 | 2.12 | 0.16 | 2.38 | 2.02 | 6.67 |
| Synthetic Example 4 | 6.13 | 0.30 | 7.57 | 5.44 | 19.43 |
| Synthetic Example 5 | 3.50 | 0.58 | 4.67 | 5.15 | 13.89 |

[a] The formulation of the accord is at 0.3 wt % and is composed as follows: 10 wt % Methyl nonyl acetaldehyde, 40 wt % P.T. Bucinal, 20 wt % Precyclemone B, and 30 wt % Floralozone.

As shown in Table 3, modified amino acid compounds provide an advantage in detergent compositions. In this data set Synthetic Examples 4 and 5 have improved benefits over synthetic example 3. Where the trimeric structure of synthetic example 4 yielded the highest headspace. No clear trend is obtained between individual benefit agents across the tested series.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A treatment composition comprising:
a treatment adjunct, and
0.001% to 30% by weight of the treatment composition of a modified amino acid multimer compound,
wherein the multimer compound comprises a central linking group and from two to six amino acid portions each covalently linked to the central linking group by a heteroatom selected from the group consisting of O, S, and N,
wherein the central linking group comprises from 3 to 18 carbon atoms,
wherein the central linking group does not comprise a peptide bond,
wherein each amino acid portion comprises a carbon backbone comprising one or more carbon atoms, a carbonyl group that comprises a carbon atom, and a nitrogen atom,
wherein the heteroatom is part of the central linking group and is directly bonded to the carbon atom of the carbonyl group of the amino acid portion,
wherein at least one amino acid portion comprises an organic moiety
covalently bonded to the nitrogen atom of the amino acid portion,
wherein the organic moiety comprises a benefit agent residue,
wherein when one or more bonds that connect the benefit agent residue to the amino acid portion are cleaved, a benefit agent is released,
wherein the benefit agent comprises an aldehyde moiety, a ketone moiety, or a combination thereof.

2. The treatment composition according to claim 1, wherein the carbon backbone of each amino acid portion independently comprises from 1 to 9 carbon atoms.

3. The treatment composition according claim 1, wherein at least one of the amino acid portions are derived from proteogenic amino acids.

4. The treatment composition according to claim 1, wherein the amino acid portions are derived from proteogenic amino acids having the same identity.

5. The treatment composition according to claim 1, wherein at least two of the amino acid portions comprise a benefit agent residue.

6. A treatment composition comprising:
a treatment adjunct, and
0.001% to 30% by weight of the treatment composition of a modified amino acid multimer compound,
wherein the multimer compound comprises a central linking group and from two to six amino acid portions each covalently linked to the central linking group,
wherein the central linking group comprises from 3 to 18 carbon atoms,
wherein the central linking group does not comprise a peptide bond,
wherein each amino acid portion comprises a carbonyl group at a C terminus, wherein the carbonyl group comprises a carbon atom,
wherein the carbon atom of the carbonyl is bonded to a heteroatom of the central linking group,
wherein the heteroatom is selected from the group consisting of O, S, and N,
wherein each amino acid portion further comprises a nitrogen atom at an N terminus, wherein at least one amino acid portion comprises a benefit agent residue that is bonded to the nitrogen atom at the N terminus of the at least one amino acid portion, wherein a benefit agent is released when one or more bonds that connect the benefit agent residue to the amino acid portion are cleaved, wherein the benefit agent comprises an aldehyde moiety, a ketone moiety, or a combination thereof.

7. The treatment composition according to claim 6, wherein the carbon backbone of each amino acid portion independently comprises from 1 to 9 carbon atoms.

8. The treatment composition according to claim 6, wherein at least one of the amino acid portions are derived from proteogenic amino acids.

9. The treatment composition according to claim 6, wherein the amino acid portions are derived from proteogenic amino acids having the same identity.

10. The treatment composition according to claim 6, wherein at least two of the amino acid portions comprise a benefit agent residue.

11. A treatment composition comprising:

a treatment adjunct, and 0.001% to 30% by weight of the treatment composition of a modified amino acid multimer compound, wherein the modified amino acid multimer compound is characterized by a structure according to Formula I:

$$L[E]_t \quad \text{Formula I,}$$

wherein t is independently an integer from 2 to 6;

wherein L is a central linking group that is multivalent and that comprises 3 to 18 carbon atoms;

wherein the central linking group does not comprise a peptide bond;

wherein each E group is independently selected from -GH, -GX, or a moiety according to Formula II:

Formula II

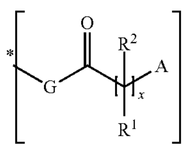

with the proviso that the multimer compound comprises at least two E groups that are moieties according to Formula II, wherein * indicates the point of attachment of the E group with L, wherein the value of x is from 1 to 9, wherein each G is independently selected from the group consisting of —O—, —N($R^3$)—, and —S—, wherein each $R^3$, if present, is independently selected from H or a monovalent moiety with a molecular weight between 14 and 881 Da, wherein X, if present, is a suitable charge-balancing counterion, wherein each $R^1$ is independently selected from H or a monovalent moiety with a molecular weight between 15 and 507 Da, wherein each $R^2$ is independently selected from H and a monovalent moiety with a molecular weight of between 15 and 1000 Da, wherein each A group is a monovalent nitrogen-comprising moiety, wherein at least one A group comprises an independently selected benefit agent residue that is linked to the rest of the A group by one or more bonds, wherein a benefit agent is released when the one or more bonds are cleaved, wherein the benefit agent comprises an aldehyde moiety, a ketone moiety, or a combination thereof.

12. The treatment composition according to claim 11, wherein each A group is independently selected from the group consisting of:

(a) $H_2N$—;

(b) ZN—, wherein  represents a linking bond between the nitrogen atom and a carbon atom of the Z group, wherein the linking bond is one of:

(i) a double bond, thereby forming an imine bond, or (ii) a single bond formed from a 1,4-addition when the benefit agent from which the benefit agent residue is derived comprises an alpha-beta unsaturated carbonyl-containing moiety that is an aldehyde moiety or a ketone moiety, wherein the nitrogen atom of the Z**N— group is further bonded to a hydrogen (—H);

(c) HG'$(J)_d$N(H)—; and (d)

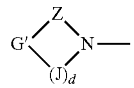

wherein the index d is selected from 1 to 3;

wherein each G' is independently selected from —O—, —S—, or —N($R^7$)—, wherein each $R^7$, if present, is independently selected from —H or a monovalent moiety with a molecular weight of from about 15 to about 255 Da, wherein the Z group comprises from 4 to 34 carbon atoms, and wherein the N and the G' are bonded to the same carbon atom of the Z group, wherein each J is independently selected from the group consisting of $C(R^9)_2$, —O—, and —N($R^9$), wherein each $R^9$ is independently selected from H or a monovalent moiety with a molecular weight between 14 and 990 Da, with the proviso that a first $R^9$ and a second $R^9$ can be taken together, where feasible, as a divalent substituent, wherein the divalent substituent is selected from the group consisting of a fused ring, a spirocyclic ring, and an unsaturated substituent selected from the group consisting of =N($R^7$), —O, and =S, wherein $R^7$, if present, is as defined above, wherein at least one A group is independently selected from (b) or (d), wherein each Z group is the independently selected benefit agent residue.

13. The treatment composition according to claim 12, wherein at least one A group is: ZN—, and wherein the Z group of the ZN-moiety is independently selected from the group consisting of

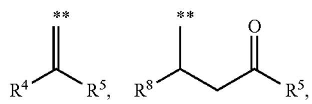

and mixtures thereof, wherein the $=C(R^4)(R^5)$ and $-CH(R^8)CH_2C(O)R^5$ moieties each represent a residue of a benefit agent, wherein the residue of the benefit agent has a molecular formula that differs from the molecular formula of the benefit agent only by having one less O atom or one more H atom, wherein the benefit agent comprises an aldehyde moiety, a ketone moiety, or a combination thereof, wherein $R^4$ is independently selected from a monovalent organic moiety, and wherein $R^5$ and $R^8$ are independently selected from the group consisting of hydrogen and a monovalent organic moiety, with the proviso that $R^4$ and $R^5$, or $R^8$ and $R^5$, may combine to form a cyclic divalent organic moiety.

14. The treatment composition according to claim 12, wherein the Z group is a benefit agent residue having the following structure:

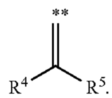

15. The treatment composition according to claim 11, wherein at least one of the following is true:

more than one A group comprises a benefit agent residue;

for a given compound, the identity of the A groups are identical;

for a given compound, the identity of the A groups are different;

wherein for a given compound, the identity of the Z groups are identical; and/or wherein for a given compound, the identity of the Z groups are different.

16. The treatment composition according to claim 12, wherein at least one $R^2$ comprises a residue of an additional benefit agent, wherein the $R^2$ that comprises the residue is a monovalent moiety with a molecular weight of from 54 and 1000 Da.

17. The treatment composition according to claim 12, wherein the central linking group comprises from 3 to 16 carbon atoms.

18. The treatment composition according to claim 12, wherein the central linking group is a divalent, trivalent, or tetravalent organic moiety.

19. The treatment composition according to claim 12, wherein the central linking group is derived from a polyhydric alcohol selected from a diol, a triol, or pentaerythritol.

20. The treatment composition according to claim 12, wherein the benefit agent residue is a residue of a benefit agent selected from a perfume raw material, an antimicrobial agent, a pesticide, an insect repellant, an anti-fungal agent, a herbicidal agent, a hueing dye, an antioxidant, a non-perfume organoleptic, or a combination thereof.

* * * * *